(12) United States Patent
Watanabe et al.

(10) Patent No.: US 9,468,556 B2
(45) Date of Patent: Oct. 18, 2016

(54) DEFORMED NAIL CORRECTOR

(71) Applicants: Maruho Co., Ltd., Osaka-shi, Osaka (JP); Maruho Hatsujyo Kogyo Co., Ltd., Kyoto-shi, Kyoto (JP)

(72) Inventors: Hideki Watanabe, Kyoto (JP); Yoshihiro Nakahashi, Kyoto (JP); Chieko Tanaka, Kyoto (JP); Tomoyuki Fujita, Kyoto (JP); Masahiro Takeuchi, Kyoto (JP); Yasuyuki Hitomi, Kyoto (JP)

(73) Assignees: Maruho Co., Ltd., Osaka-shi, Osaka (JP); Maruho Hatsujyo Kogyo Co., Ltd., Kyoso-shi, Kyoto (JP)

( * ) Notice: Subject to any disclaimer, the term of this patent is extended or adjusted under 35 U.S.C. 154(b) by 0 days.

(21) Appl. No.: 14/425,198

(22) PCT Filed: Aug. 30, 2013

(86) PCT No.: PCT/JP2013/073375
§ 371 (c)(1),
(2) Date: Mar. 2, 2015

(87) PCT Pub. No.: WO2014/034876
PCT Pub. Date: Mar. 6, 2014

(65) Prior Publication Data
US 2015/0230967 A1 Aug. 20, 2015

(30) Foreign Application Priority Data
Aug. 31, 2012 (JP) .................................. 2012-191628

(51) Int. Cl.
*A61F 5/00* (2006.01)
*A61F 5/11* (2006.01)

(52) U.S. Cl.
CPC ....................................... *A61F 5/11* (2013.01)

(58) Field of Classification Search
CPC ....... E04H 15/44; E04H 15/48; E04H 15/64; A61B 17/683; A61B 17/685; A61B 17/686; A61B 17/848; A61B 17/864; A61B 17/8863; A61B 17/8869; A61B 2017/565; A61B 2017/681; A61B 2562/182; A61B 17/68; A61B 5/6804; A61B 2017/1775; A61B 5/0002; A61B 5/0022; A61B 5/02055; A61B 5/04085; A61B 5/1135; A61B 17/0401; A61B 17/8061; A61B 17/8085; A61B 17/82; A61B 17/842
USPC ....................................................... 602/30–31
See application file for complete search history.

(56) References Cited

U.S. PATENT DOCUMENTS 3,583,397 A * 6/1971 Baddour .................... A61F 5/04
24/710.8
4,566,208 A * 1/1986 Shaffner ............... A61F 13/041
36/110

(Continued)

FOREIGN PATENT DOCUMENTS

DE  10 2006 018 987 A1  10/2007
EP      1 849 442 A1      10/2007

(Continued)

OTHER PUBLICATIONS

International Preliminary Report on Patentability for PCT Application No. PCT/JP2013/073375 dated Mar. 3, 2015.
Extended European Search Report for European Application No. 13933346.3 dated Mar. 10, 2016.

*Primary Examiner* — Michael Brown
(74) *Attorney, Agent, or Firm* — Muncy, Geissler, Olds & Lowe, P.C.

(57) ABSTRACT

A deformed nail corrector for correcting a deformed nail is provided that includes: a first elastic wire which has one end portion thereof fixed to one edge of the deformed nail in a width direction; a second elastic wire which has one end portion thereof fixed to the other edge of the deformed nail in the width direction; and a binding means which binds the first and second elastic wires to each other and is slidable along the first and second elastic wires in a bound state. The first and second elastic wires are brought into a state where the first and second wires are deformed along the deformed nail with the first and second, elastic wires being in a corrector mounting state where the first and second elastic wires are bound to each other by the binding means.

14 Claims, 20 Drawing Sheets

(56) References Cited

U.S. PATENT DOCUMENTS

| | | | | |
|---|---|---|---|---|
| 5,012,799 A | * | 5/1991 | Remmen | A61F 5/11 602/30 |
| 8,517,966 B2 | * | 8/2013 | Erdogan | A61F 5/11 602/23 |
| 2004/0260221 A1 | * | 12/2004 | Machida | A61F 5/11 602/30 |
| 2012/0238930 A1 | | 9/2012 | Yoshino et al. | |

FOREIGN PATENT DOCUMENTS

| | | |
|---|---|---|
| EP | 1 158 881 A1 | 3/2010 |
| EP | 2 508 154 A1 | 10/2012 |
| FR | 2 939 638 A1 | 6/2010 |
| JP | 2007-289712 A | 11/2007 |
| JP | 2011-98081 | 5/2011 |
| WO | WO 2011/064889 A1 | 6/2011 |

\* cited by examiner

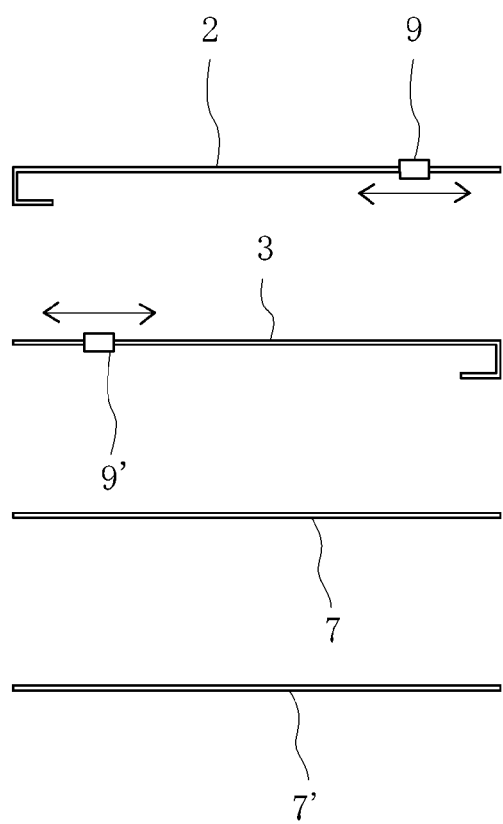

DEFORMED NAIL CORRECTOR

This application is a National Stage of International Application No. PCT/JP2013/073375, filed on Aug. 30, 2013, for which priority is claimed under 35 U.S.C. §120; and this application claims priority of Japanese Application No. 2012491628 filed in Japan on Aug. 31, 2012 under 35 U.S.C. §119; the entire contents of all are hereby incorporated by reference.

TECHNICAL FIELD

The present invention relates to a deformed nail corrector for correcting a deformed nail such as a curl nail or an ingrown nail.

BACKGROUND ART

Conventionally, as a deformed nail corrector for correcting a deformed nail such as a curl nail or an ingrown nail, there has been known a nail corrector which includes: two elastic plates each of which has one end portion thereof folded in a hook shape and has an L-shaped cross bar welded to a portion thereof in the vicinity of the one end portion; and a thread which binds these two elastic plates to each other (see Patent Document 1, for example).

When mounting this deformed nail corrector on a deformed nail, firstly, one end portion of one of the two elastic plates is hooked and fixed to one edge of the deformed nail in the width direction, and one end portion of the other elastic plate is hooked and fixed to the other edge of the deformed nail in the width direction. Then, the other end portion of one elastic plate is fitted into a space below the cross bar of the other elastic plate, and the other end portion of the other elastic plate is fitted into a space below the crossbar of one elastic plate. Lastly, threads are engaged with the respective cross bars so that two elastic plates are fastened to each other, thus mounting the deformed nail corrector on the deformed nail. When the deformed nail corrector is mounted on the deformed nail, two elastic plates are brought into a state where these elastic plates are bent along the deformed nail so that an elastic force (a force which makes the elastic plates return to an original shape) is generated in two elastic plates. By maintaining this elastic force for a long period, the deformed nail can be corrected.

PRIOR ART DOCUMENT

Patent Document

Patent Document 1: JP-A-2011-98081

SUMMARY OF THE INVENTION

Problems to be Solved by the Invention

In the above-mentioned conventional deformed nail corrector, when an elastic force is excessively large, the deformed nail is excessively corrected thus causing a possibility of cracking, chipping or the like occur in the deformed nail. On the other hand, when the elastic force is excessively small, there is a possibility that it takes a long period for correcting the deformed nail or the deformed nail cannot be sufficiently corrected. In view of the above, it is desirable that magnitude of the elastic force can be adjusted corresponding to a state of the deformed nail.

However, in the above-mentioned conventional deformed nail corrector, the cross bar is welded to the elastic plate, and hence, in order to adjust the magnitude of an elastic force, it is necessary to use another elastic plate on which a cross bar is welded at a different position or to use a different elastic plate having a different thickness. That is, in the above-mentioned conventional deformed nail corrector, it is necessary to prepare many kinds of elastic plates in advance, and it is also necessary to connect a thread again each time the elastic plate is exchanged, and hence, the adjustment of magnitude of an elastic force requires an extra cost and extra time and efforts.

The present invention has been made in view of the above-mentioned circumstances, and it is an object of the present invention to provide a deformed nail corrector which enables a user to adjust magnitude of an elastic force without spending an extra cost and extra time and efforts.

Means for Solving the Problems

To overcome the above-mentioned drawbacks, a deformed nail corrector according to the present invention is directed to (1) a deformed nail corrector for correcting a deformed nail, the deformed nail corrector which includes: a first elastic wire which has one end portion thereof fixed to one edge of the deformed nail in a width direction; a second elastic wire which has one end portion thereof fixed to the other edge of the deformed nail in the width direction; and a binding means which binds the first and second elastic wires to each other and is slidable along the first and second elastic wires in a bound state, wherein the first and second elastic wires are brought into a state where the first and second wires are deformed along the deformed nail in a corrector mounting state where one end portion of the first elastic wire is fixed to one edge of the deformed nail in the width direction, one end portion of the second elastic wire is fixed to the other edge of the deformed nail in the width direction, and the first and second elastic wires are bound to each other by the binding means.

Due to such a configuration, an elastic force of the first elastic wire and an elastic force of the second elastic wire can be adjusted while holding the corrector mounting state by adjusting the binding position by sliding the binding means in the corrector mounting state.

The term "elastic wire" in the present invention means a wire which generates an elastic force. This "elastic wire" also includes, in its category, not only a wire made of an elastic alloy but also a wire made of a super elastic alloy which intends to return to an original shape completely (100%).

(2) In the above-mentioned deformed nail corrector (1), it is preferable that the binding means includes two or more sliders which are slidable independently from each other along the first and second elastic wires in the corrector mounting state.

Due to such a configuration, an elastic force of the first elastic wire and an elastic force of the second elastic wire can be adjusted while holding the corrector mounting state by adjusting a distance between the sliders in the corrector mounting state. To be more specific, the elastic force of the first elastic wire and the elastic force of the second elastic wire can be increased by increasing the distance between the sliders, while the elastic force of the first elastic wire and the elastic force of the second elastic wire can be decreased by narrowing the distance between the sliders.

(3) In the above-mentioned deformed nail corrector (2), the slider may have: a first through hole through which the first elastic wire is to be inserted; and a second through hole through which the second elastic wire is to be inserted.

(4) In the above-mentioned deformed nail corrector (3), the slider may have: a first slit which is communicated with the first through hole, the first slit enabling fixing of the slider to the first elastic wire in the corrector mounting state; and a second slit which is communicated with the second through hole, the second slit enabling fixing of the slider to the second elastic wire in the corrector mounting state, and the first elastic wire may be inserted into the inside of the first through hole through the first slit or the second elastic wire is inserted into the inside of the second through hole through the second slit.

(5) In the above-mentioned deformed nail corrector (3), the first elastic wire may be formed of two or more independent elastic wires, and the first through hole may be formed of two or more independent through holes through which the respective elastic wires of the first elastic wire are to be inserted.

(6) In the above-mentioned deformed nail corrector (5), the second elastic wire may be formed of two or more independent elastic wires, and the second through hole may be formed of two or more independent through holes through which the respective elastic wires of the second elastic wire are to be inserted.

(7) In the above-mentioned deformed nail corrector (1), one end portion of the first elastic wire and one end portion of the second elastic wire may be folded in a hook shape.

(8) In the above-mentioned deformed nail correctors (3) to (6), it is preferable that the deformed nail corrector further includes a third elastic wire whose both end portions are not fixed to one edge of the deformed nail in the width direction or the other edge of the deformed nail in the width direction, the slider further has a third through hole through which the third elastic wire is to be inserted, and the first, second and third elastic wires are brought into a state where the first, second and third wires are deformed along the deformed nail in a corrector mounting state where one end portion of the first elastic wire is fixed to one edge of the deformed nail in the width direction, one end portion of the second elastic wire is fixed to the other edge of the deformed nail in the width direction, and the first, second and third elastic wires are bound to each other by the slider.

Due to such a configuration, an elastic force generated in the deformed nail can be increased by an amount of elastic force generated by the third elastic wire. On the other hand, the elastic force can be decreased by removing the third elastic wire. That is, due to such a configuration, an elastic force generated in the deformed nail can be adjusted over a wide range by removing or mounting the third elastic wire depending on a state of the deformed nail.

(9) In the above-mentioned deformed nail corrector (8), the slider may have a third slit which is communicated with the third through hole, the third slit enabling fixing of the slider to the third elastic wire in the corrector mounting state.

(10) In the above-mentioned deformed nail corrector (9), the third elastic wire may be inserted through the third through hole through the third slit.

(11) In the above-mentioned deformed nail corrector (8), the third elastic wire may be arranged between the first elastic wire and the second elastic wire in a length direction of the deformed nail in the corrector mounting state.

(12) In the above-mentioned deformed nail corrector (8), the first elastic wire may be arranged between the second elastic wire and the third elastic wire in a length direction of the deformed nail in the corrector mounting state.

(13) In the above-mentioned deformed nail corrector (8), the third elastic wire may be formed of two or more independent elastic wires, and the third through hole is formed of two or more independent through holes through which the respective elastic wires of the third elastic wire are to be inserted.

(14) In the above-mentioned deformed nail corrector (3), the first and second through holes may be formed parallel to each other in a thickness direction of the slider.

(15) In the above-mentioned deformed nail corrector (13), the first and second through holes may be formed parallel to each other in a thickness direction of the slider, two or more independent through holes which constitute the third through hole may be formed parallel to each other in the thickness direction, and the first through hole, the second through hole and two or more independent through holes may be arranged parallel to each other in a direction orthogonal to the thickness direction.

Effect of the Invention

According to the present invention, it is possible to provide a deformed nail corrector which enables a user to adjust magnitude of an elastic force without spending an extra cost and extra time and efforts.

BRIEF DESCRIPTION OF THE DRAWINGS

FIG. 12 is a view showing a deformed nail corrector according to a fifth embodiment of the present invention.

MODE FOR CARRYING OUT THE INVENTION

Hereinafter, preferred embodiments of a deformed nail corrector according to the present invention are described by reference to attached drawings.

First Embodiment

Figure 1:
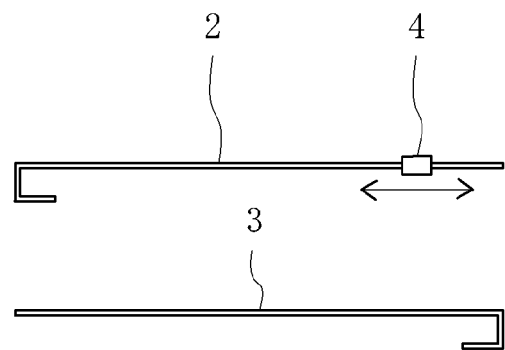
FIG. 1 is a view showing a deformed nail corrector according to a first embodiment of the present invention.

FIG. 1 shows a deformed nail corrector 1A according to a first embodiment of the present invention. The deformed nail corrector 1A according to this embodiment is provided for correcting a deformed nail such as a curl nail or an ingrown nail (particularly, a deformed nail of a foot). As shown in the figure, the deformed nail corrector 1A includes: a first elastic wire 2 made of a Ti—Al—V alloy; a second elastic wire 3 made of a Ti—Al—V alloy; and one slider (corresponding to "binding means" of the present invention) 4 made of Ti.

The first elastic wire 2 and the second elastic wire 3 are straight linear elastic wire, and have one end portion thereof folded in a hook shape. The first elastic wire 2 and the second elastic wire 3 have a rectangular cross section. The slider 4 is slidably mounted on the first elastic wire 2.

Figure 2:
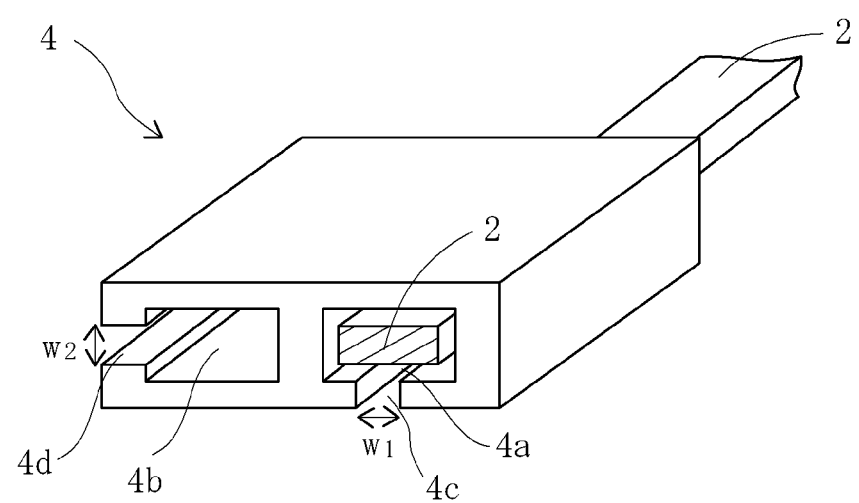
FIG. 2 is a perspective view of a slider according to the first embodiment of the present invention.

As shown in FIG. 2, the slider 4 has: a first through hole 4a through which the first elastic wire 2 is to be inserted; a second through hole 4b through which the second elastic wire 3 is to be inserted; a first slit 4c which is communicated with the first through hole 4a; and a second slit 4d which is communicated with the second through hole 4b. In the slider 4, a side where the first slit 4c is formed constitutes a side (lower side) which is in contact with a deformed nail.

The first through hole 4a and the second through hole 4b have rectangular cross sections (opening faces) which are one size larger than cross-sectional shapes of the first elastic wire 2 and the second elastic wire 3 such that the slider 4 is smoothly slidable along the first elastic wire 2 and the second elastic wire 3. However, the long side of the first elastic wire 2 in a cross-sectional shape is longer than the short side of the first through hole 4a in a cross-sectional shape, and hence, the first elastic wire 2 is not rotatable in the first through hole 4a. In the same manner, the long side of the second elastic wire 3 in a cross-sectional shape is longer than the short side of the second through hole 4b in a cross-sectional shape, and hence, the second elastic wire 3 is not also rotatable in the second through hole 4b.

A width $w_1$ of the first slit 4c is longer than the short side of the first elastic wire 2 in a cross-sectional shape, and is shorter than the long side of the first elastic wire 2 in a cross-sectional shape. In the same manner, a width $w_2$ of the second slit 4d is longer than the short side of the second elastic wire 3 in a cross-sectional shape, and is shorter than the long side of the second elastic wire 3 in a cross-sectional shape. Further, the first slit 4c is formed on a lower side of the first through hole 4a (the long side in a cross-sectional shape), and the second slit 4d is formed on the left side of the second through hole 4b (the short side in a cross-sectional shape). Accordingly, while the second elastic wire 3 can be inserted through the second through hole 4b or the second elastic wire 3 can be taken out from the second through hole 4b through the second slit 4d, it is neither possible to insert the first elastic wire 2 through the first through hole 4a nor possible to take out the first elastic wire 2 from the first through hole 4a through the first slit 4c.

Figure 3A:
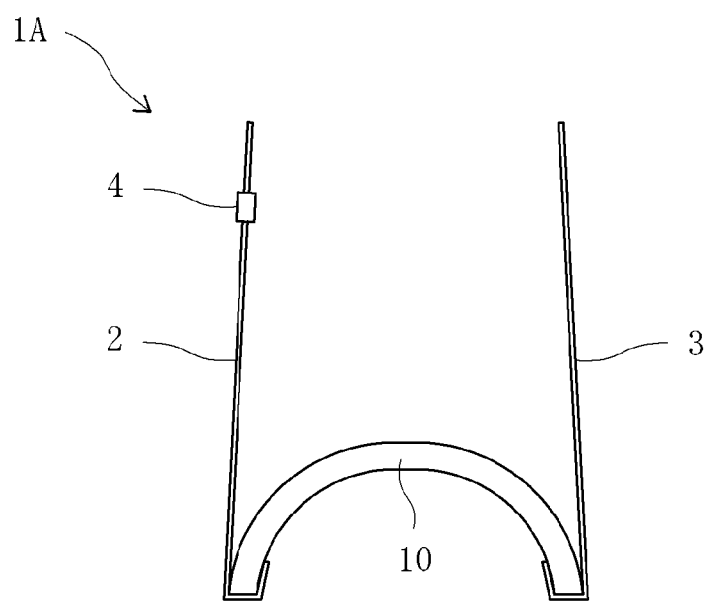
FIG. 3A to FIG. 3C are views for explaining steps of mounting the deformed nail corrector according to the first embodiment.
Figure 3B:
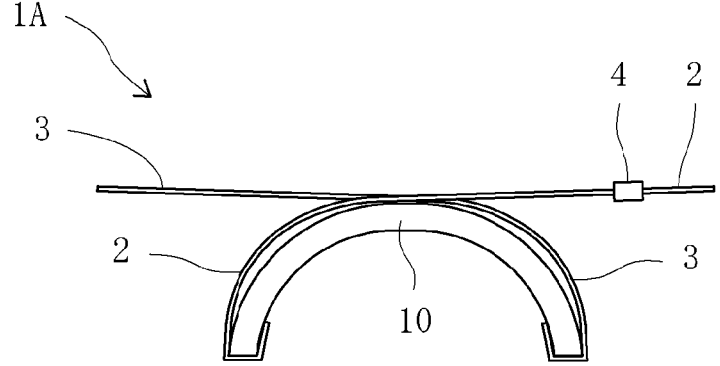
Figure 3C:
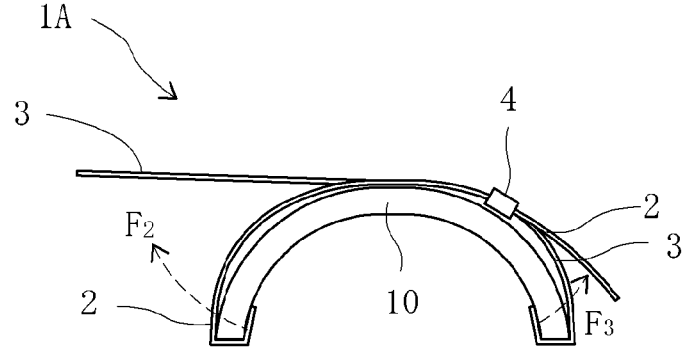

The deformed nail corrector 1A according to this embodiment is mounted on the deformed nail 10 in accordance with steps shown in FIG. 3A to FIG. 3C. In the following description, it is assumed that the deformed nail 10 is a largely bent curl nail.

Firstly, a nail softening agent (for example, a deformed nail correcting processing agent described in JP-A-2004-238288) is applied to a surface of the deformed nail 10 by coating and, thereafter, as shown in FIG. 3A, one end portion of the first elastic wire 2 is hooked and fixed to one edge of the deformed nail 10 in the width direction, and one end portion of the second elastic wire 3 is hooked and fixed to the other edge of the deformed nail 10 in the width direction.

Next, as shown in FIG. 3B, the first elastic wire 2 and the second elastic wire 3 are bent along the deformed nail 10.

Next, as shown in FIG. 3C, the first elastic wire 2 is further bent, and the second elastic wire 3 is to be inserted through the second through hole 4b through the second slit 4d formed in the slider 4. Accordingly, the first elastic wire 2 and the second elastic wire 3 are bound to each other by the slider 4, and hence, a state where the first elastic wire 2 and the second elastic wire 3 are bent (deformed) along the deformed nail 10 is maintained. As a result, an elastic force $F_2$ is generated at one edge of the deformed nail 10 in the width direction by the first elastic wire 2, and an elastic force $F_3$ is generated at the other edge of the deformed nail 10 in the width direction by the second elastic wire 3. When the first elastic wire 2 and the second elastic wire 3 are excessively long, the other end portion side of the first elastic wire 2 and the other end portion side of the second elastic wire 3 may be cut.

In the deformed nail corrector 1A according to this embodiment, by sliding the slider 4 along the first elastic wire 2 and the second elastic wire 3 in a corrector mounting state shown in FIG. 3C, elastic forces $F_2$, $F_3$ can be adjusted. To be more specific, by sliding the slider 4 toward the other edge side of the deformed nail 10 in the width direction (one end portion side of the second elastic wire 3) in a corrector mounting state, an elastic force $F_3$ of the second elastic wire 3 can be decreased and an elastic force $F_2$ of the first elastic wire 2 can be increased. On the other hand, by bringing the slider 4 closer to one edge side of the deformed nail 10 in the width direction (one end portion side of the first elastic wire 2), an elastic force $F_2$ of the first elastic wire 2 can be decreased, and an elastic force $F_3$ of the second elastic wire 3 can be increased.

In the deformed nail corrector 1A according to this embodiment, the first slit 4c and the second slit 4d are formed in the slider 4, and hence, the slider 4 can be fixed by caulking to the first elastic wire 2 and the second elastic wire 3 by depressing the slider 4 by a nipper or the like after adjusting elastic forces $F_2$, $F_3$. Although elastic forces $F_2$, $F_3$ cannot be readjusted after the slider 4 is fixed by caulking, the deformed nail corrector 1A can generate elastic forces $F_2$, $F_3$ in a stable manner for a long period. Further, in the deformed nail corrector 1A according to this embodiment, even when the slider 4 is fixed by caulking to only either one of the first elastic wire 2 and the second elastic wire 3, elastic forces $F_2$, $F_3$ can be generated in a stable manner. When the slider 4 is fixed by caulking only to the first elastic wire 2, the second elastic wire 3 can be removed through the second slit 4d.

In the deformed nail corrector 1A according to this embodiment, the slider 4 can be fixed to the first elastic wire 2 and the second elastic wire 3 by an adhesive agent in such a manner that the adhesive agent is injected into the first through hole 4a and the second through hole 4b in place of fixing by caulking. Further, the slider 4 may be fixed to the first elastic wire 2 and the second elastic wire 3 by welding or screwing by making use of the first slit 4c and the second slit 4d.

Second Embodiment

Figure 4:
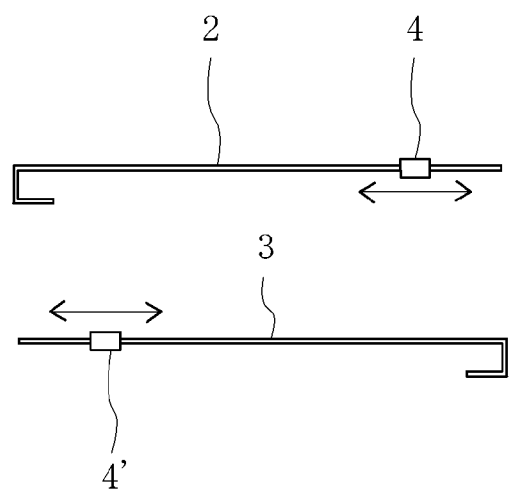
FIG. 4 is a view showing a deformed nail corrector according to a second embodiment of the present invention.

FIG. 4 shows a deformed nail corrector 1B according to a second embodiment of the present invention. As shown in FIG. 4, the deformed nail corrector 1B according to this embodiment has the substantially same configuration as the deformed nail corrector 1A according to the first embodiment except for that a slider 4' is slidably mounted on a second elastic wire 3.

Figure 5:
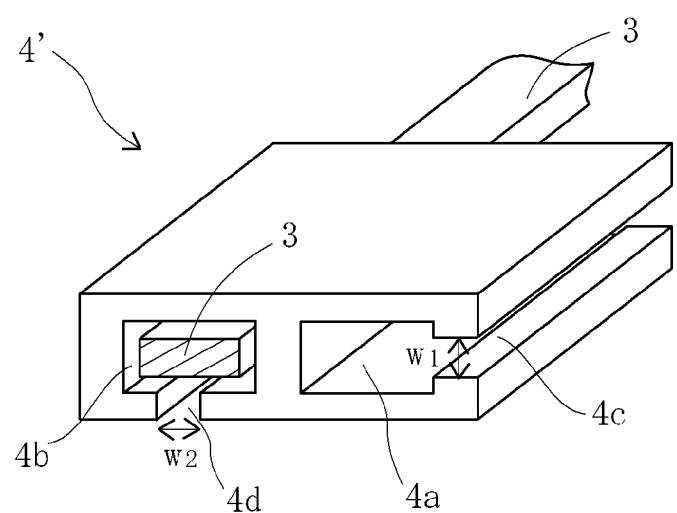
FIG. 5 is a perspective view of a slider according to the second embodiment of the present invention.

FIG. 5 is a perspective view of the slider 4' as viewed from the same direction as FIG. 2. As shown in FIG. 5, the slider 4' has: a first through hole 4a through which the first elastic wire 2 is to be inserted; a second through hole 4b through which the second elastic wire 3 is to be inserted; a first slit 4c which is communicated with the first through hole 4a; and a second slit 4d which is communicated with the second through hole 4b. That is, the slider 4' and the slider 4 differ from each other only with respect to the position of the first slit 4c and the position of the second slit 4d.

The first slit 4c is formed on the right side of the first through hole 4a (the short side in a cross-sectional shape), and the second slit 4d is formed on the lower side of the second through hole 4b (the long side in a cross-sectional shape). Accordingly, while the first elastic wire 2 can be inserted through the first through hole 4a or the first elastic wire 2 can be taken out from the first through hole 4a through the first slit 4c, it is neither possible to insert the second elastic wire 3 through the second through hole 4b nor possible to take out the second elastic wire 3 from the second through hole 4b through the second slit 4d.

Figure 6A:
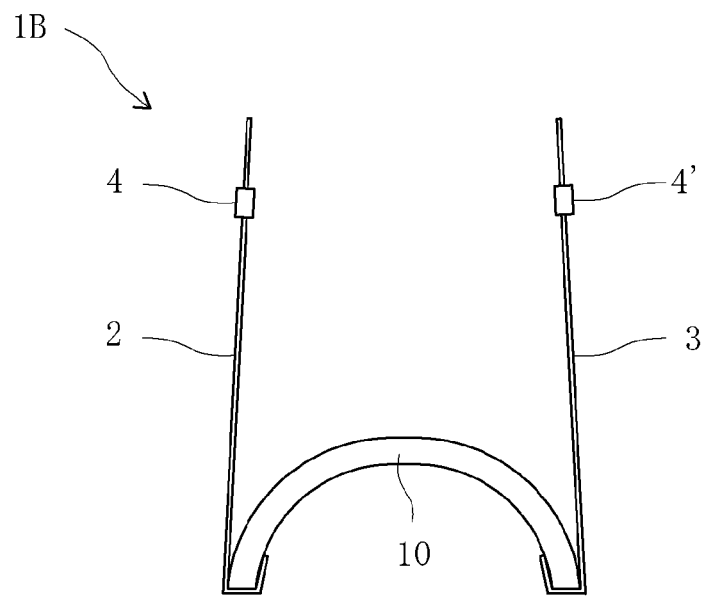
FIG. 6A to FIG. 6C are views for explaining steps of mounting the deformed nail corrector according to the second embodiment.
Figure 6B:
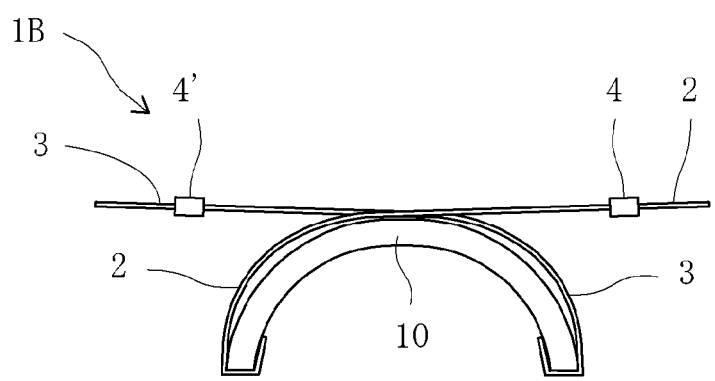
Figure 6C:
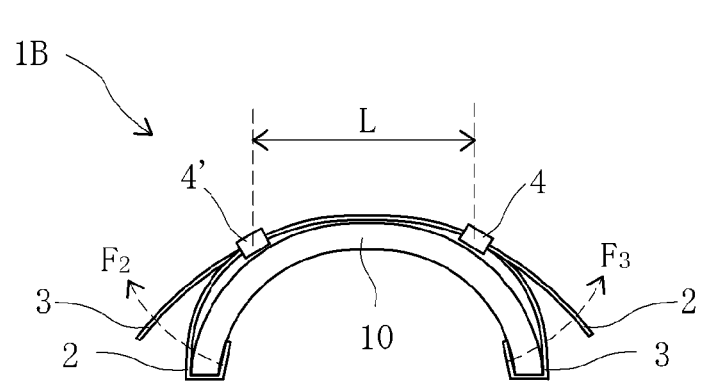

The deformed nail corrector 1B according to this embodiment is mounted on the deformed nail 10 in accordance with steps shown in FIG. 6A to FIG. 6C.

Firstly, a nail softening agent is applied to a surface of the deformed nail 10 by coating and, thereafter, as shown in FIG. 6A, one end portion of the first elastic wire 2 is hooked and fixed to one edge of the deformed nail 10 in the width direction, and one end portion of the second elastic wire 3 is hooked and fixed to the other edge of the deformed nail 10 in the width direction.

Next, as shown in FIG. 6B, the first elastic wire 2 and the second elastic wire 3 are bent along the deformed nail 10.

Next, as shown in FIG. 6C, the first elastic wire 2 and the second elastic wire 3 are further bent, the second elastic wire 3 is to be inserted through the second through hole 4b through the second slit 4d formed in the slider 4, and the first elastic wire 2 is to be inserted through the first through hole 4a through the first slit 4c formed in the slider 4'. Accordingly, the first elastic wire 2 and the second elastic wire 3 are bound to each other by the sliders 4, 4', and hence, a state where the first elastic wire 2 and the second elastic wire 3 are bent (deformed) along the deformed nail 10 is maintained. As a result, an elastic force $F_2$ is generated at one edge of the deformed nail 10 in the width direction by the first elastic wire 2, and an elastic force $F_3$ is generated at the other edge of the deformed nail 10 in the width direction by the second elastic wire 3.

In the deformed nail corrector 1B according to this embodiment, by sliding the sliders 4, 4' which are slidable independently from each other along the first elastic wire 2 and the second elastic wire 3 in a corrector mounting state shown in FIG. 6C, a distance L between the sliders 4, 4' is adjusted, to thereby adjusting elastic forces $F_2$, $F_3$. To be more specific, the elastic forces $F_2$ of the first elastic wire 2 and the elastic force $F_3$ of the second elastic wire 3 can be increased by increasing the distance L between the sliders 4, 4', while the elastic force $F_2$ of the first elastic wire 2 and the elastic force $F_3$ of the second elastic wire 3 can be decreased by narrowing the distance L between the sliders 4, 4'.

Third Embodiment

Figure 7:
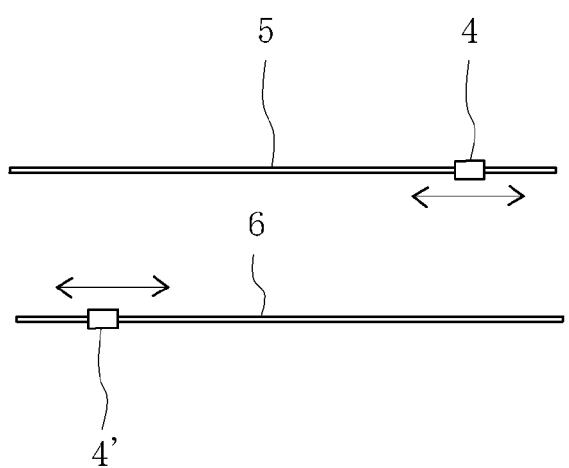
FIG. 7 is a view showing a deformed nail corrector according to a third embodiment of the present invention.

FIG. 7 shows a deformed nail corrector 1C according to a third embodiment of the present invention. As shown in FIG. 7, the deformed nail corrector 1C according to this embodiment has the substantially same configuration as the deformed nail corrector 1B according to the second embodiment except for that the deformed nail corrector 1C includes a first elastic wire 5 where one end portion is not folded and a second elastic wire 6 where one end portion is not folded.

Figure 8A:
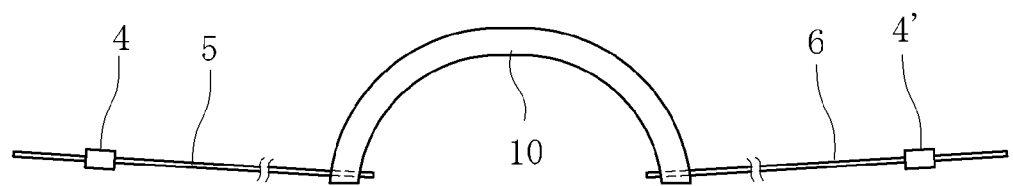
FIG. 8A to FIG. 8C are views for explaining steps of mounting the deformed nail corrector according to the third embodiment.
Figure 8B:
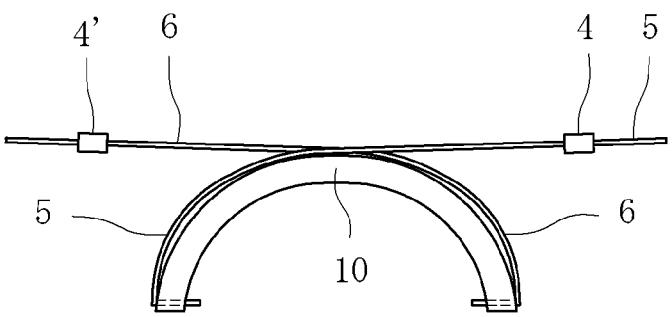
Figure 8C:
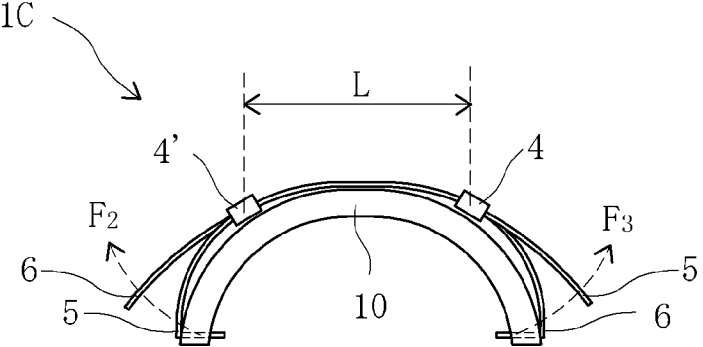

The deformed nail corrector 1C according to this embodiment is mounted on the deformed nail 10 in accordance with steps shown in FIG. 8A to FIG. 8C.

Firstly, a through hole is formed at both edges of the deformed nail 10 in the width direction and, at the same time, a nail softening agent is applied to a surface of the deformed nail 10 by coating. Thereafter, as shown in FIG. 8A, one end portion of the first elastic wire 5 is to be inserted through and fixed to the through hole formed at one edge of the deformed nail 10 in the width direction, and one end portion of the second elastic wire 6 is to be inserted through and fixed to the through hole formed at the other edge of the deformed nail 10 in the width direction.

Next, as shown in FIG. 8B, the first elastic wire 5 and the second elastic wire 6 are bent along the deformed nail 10 by folding one end portion of the first elastic wire 5 and one end portion of the second elastic wire 6.

Next, as shown in FIG. 8C, the first elastic wire 5 and the second elastic wire 6 are further bent, the second elastic wire 6 is to be inserted through the second through hole 4b through the second slit 4d formed in the slider 4, and the first elastic wire 5 is to be inserted through the first through hole 4a through the first slit 4c formed in the slider 4'. Accordingly, the first elastic wire 5 and the second elastic wire 6 are bound to each other by the sliders 4, 4'. As a result, a state where the first elastic wire 5 and the second elastic wire 6 are bent (deformed) along the deformed nail 10 is maintained so that an elastic force $F_2$ is generated at one edge of the deformed nail 10 in the width direction by the first elastic wire 5, and an elastic force $F_3$ is generated at the other edge of the deformed nail 10 in the width direction by the second elastic wire 6.

In the deformed nail corrector 1C according to this embodiment, by sliding the sliders 4, 4' which are slidable independently from each other along the first elastic wire 5 and the second elastic wire 6 in a corrector mounting state shown in FIG. 8C, a distance L between the sliders 4, 4' is adjusted. Due to such adjustment of the distance L, in the same manner as the deformed nail corrector 1B according to the second embodiment, elastic forces $F_2$, $F_3$ can be adjusted.

Fourth Embodiment

Figure 9:
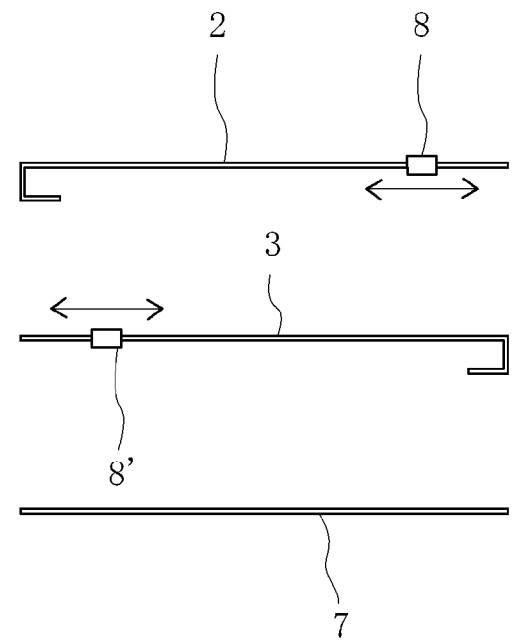
FIG. 9 is a view showing a deformed nail corrector according to a fourth embodiment of the present invention.

FIG. 9 shows a deformed nail corrector 1D according to a fourth embodiment of the present invention. As shown in FIG. 9, the deformed nail corrector 1D according to this embodiment has the substantially same configuration as the deformed nail corrector 1B according to the second embodiment except for that the deformed nail corrector 1D further includes a third elastic wire 7, and includes sliders 8, 8' in place of the sliders 4, 4'.

The third elastic wire 7 is formed of a straight linear elastic wire made of a Ti—Al—V alloy in the same manner as the first elastic wire 2 and the second elastic wire 3. However, unlike the first elastic wire 2 and the second elastic wire 3, one end portion of the third elastic wire 7 is not folded. The third elastic wire 7 has a rectangular cross-sectional shape.

Figure 10A:
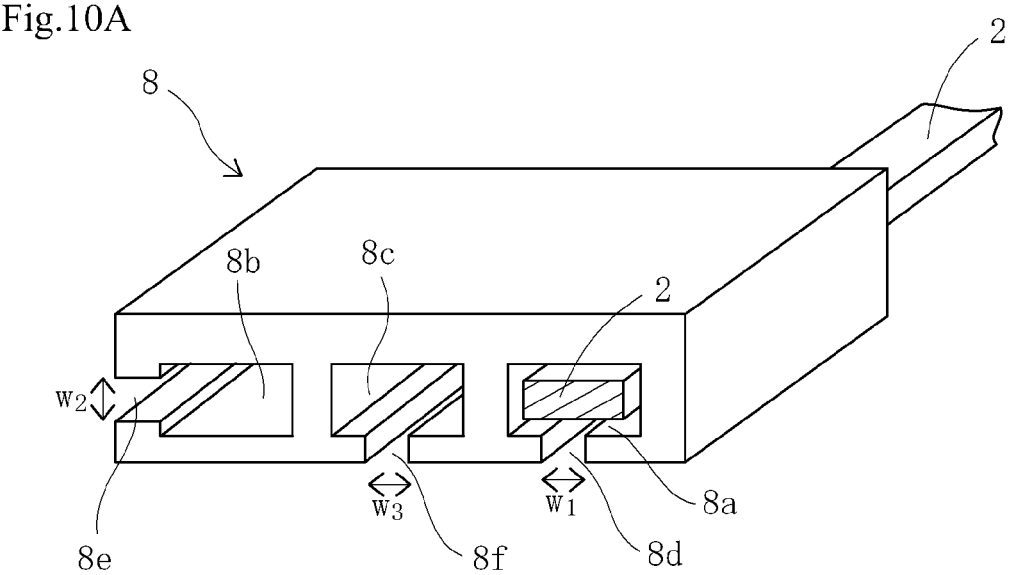
FIG. 10A and FIG. 10B are perspective views of a slider according to the fourth embodiment of the present invention.
Figure 10B:
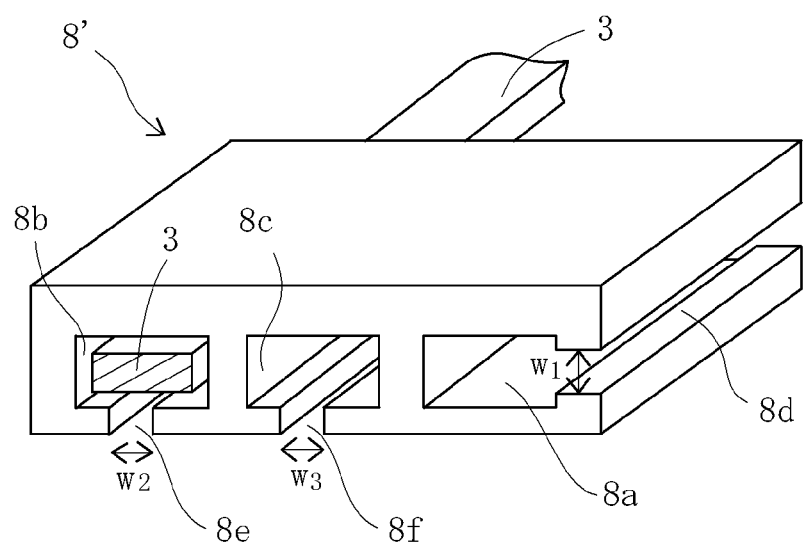

FIG. 10A is a perspective view of the slider 8, and FIG. 10B is a perspective view of the slider 8'. As shown in FIG. 10A, the slider 8 has: a first through hole 8a through which the first elastic wire 2 is to be inserted; a second through hole 8b through which the second elastic wire 3 is to be inserted; a third through hole 8c through which the third elastic wire 7 is to be inserted; a first slit 8d which is communicated with the first through hole 8a; a second slit 8e which is communicated with the second through hole 8b; and a third slit 8f which is communicated with the third through hole 8c. That is, the slider 8 is configured such that the third through hole 8c and the third slit 8f are arranged between the first through hole 4a and the second through hole 4b formed in the slider 4. The slider 8' is configured such that the third through hole 8c and the third slit 8f are arranged between the first through hole 4a and the second through hole 4b formed in the slider 4'. The slider 8 and the slider 8' differ from each other only with respect to the position of the first slit 8d and the position of the second slit 8e.

The third through holes 8c formed in the sliders 8, 8' have rectangular cross sections (opening faces) which are one size larger than a cross-sectional shape of the third elastic wire 7 such that the sliders 8, 8' are smoothly slidable along the third elastic wire 7. However, the long side of the third elastic wire 7 in a cross-sectional shape is longer than the short side of the third through hole 8c in a cross-sectional shape, and hence, the third elastic wire 7 is not rotatable in the third through hole 8c.

A width $w_3$ of the third slits 8f formed in the sliders 8, 8' respectively is longer than the short side of the third elastic wire 7 in a cross-sectional shape, and is shorter than the long side of the third elastic wire 7 in a cross-sectional shape.

Further, the third slits 8f are formed on lower sides of the third through holes 8c (the long sides in a cross-sectional shape) respectively. Accordingly, it is neither possible to insert the third elastic wire 7 through the third through hole 8c nor possible to take out the third elastic wire 7 from the third through hole 8c through the third slit 8f.

Figure 11:
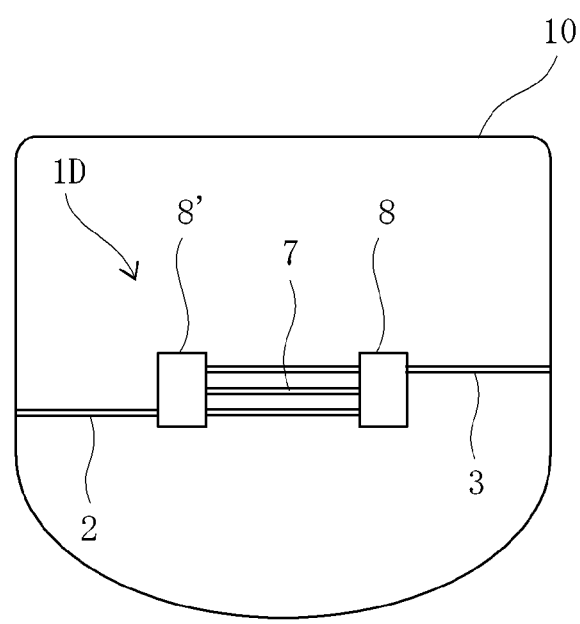
FIG. 11 is a plan view showing a mounting state of the deformed nail corrector according to the fourth embodiment.

FIG. 11 is a plan view of the deformed nail corrector 1D according to this embodiment in a state where the deformed nail corrector 1D is mounted on the deformed nail 10. As shown in FIG. 11, the third elastic wire 7 is arranged between the first elastic wire 2 and the second elastic wire 3 in the length direction of the deformed nail 10. One end portion of the first elastic wire 2 is fixed to one edge of the deformed nail 10 in the width direction, and a portion of the first elastic wire 2 projecting out of the slider 8 on the other edge portion side is cut. One end portion of the second elastic wire 3 is fixed to the other edge of the deformed nail 10 in the width direction, and a portion of the second elastic wire 3 projecting out of the slider 8' on the other edge portion side is cut. The third elastic wire 7 is arranged between the sliders 8, 8', and is not fixed to the deformed nail 10. Portions of the third elastic wire 7 projecting out of an area between the sliders 8, 8' are cut.

The deformed nail corrector 1D according to this embodiment is mounted on the deformed nail 10 in accordance with the substantially same steps as the deformed nail corrector 1B according to the second embodiment except for a step of inserting the third elastic wire 7 through the third through holes 8c formed in the sliders 8, 8'.

To be more specific, in accordance with the steps shown in FIG. 6A to FIG. 6C, the first elastic wire 2 and the second elastic wire 3 are bound to each other by the sliders 8, 8' and, thereafter, the third elastic wire 7 is to be inserted through the third through holes 8c formed in the sliders 8, 8'. Due to such an operation, the third elastic wire 7 is also bound by the sliders 8, 8', and hence, a state where the first elastic wire 2, the second elastic wire 3 and the third elastic wire 7 are bent (deformed) along the deformed nail 10 is maintained. As a result, at both edges of the deformed nail 10, an elastic force is generated also by the third elastic wire 7 in addition to elastic forces generated by the first elastic wire 2 and the second elastic wire 3.

According to the deformed nail corrector 1D according to this embodiment, compared to the deformed nail corrector 1B according to the second embodiment, an elastic force generated in the deformed nail 10 can be increased by an elastic force generated by the third elastic wire 7. On the other hand, when a large elastic force becomes unnecessary, the elastic force of the deformed nail corrector 1D according to this embodiment can be set to the substantially same level as the elastic force generated by the deformed nail corrector 1B by removing the third elastic wire 7. That is, according to the deformed nail corrector 1D according to this embodiment, an elastic force generated in the deformed nail 10 can be adjusted over a wide range by removing or mounting the third elastic wire 7 depending on a state of the deformed nail 10.

Further, in the deformed nail corrector 1D according to this embodiment, by adjusting a distance between the sliders 8, 8' by sliding the sliders 8, 8' along the first to third elastic wires 2, 3, 7, an elastic force generated in the deformed nail 10 can be also adjusted in the same manner as the deformed nail corrector 1B.

Fourth Embodiment

FIG. 12 shows a deformed nail corrector 1E according to a fifth embodiment of the present invention. As shown in FIG. 12, the deformed nail corrector 1E according to this embodiment has the substantially same configuration as the deformed nail corrector 1D according to the fourth embodiment except for that a third elastic wire is formed of two independent elastic wires 7, 7' (hereinafter referred to as third elastic wires 7, 7'), and that the deformed nail corrector 1E includes sliders 9, 9' in place of the sliders 8, 8'.

Figure 13A:
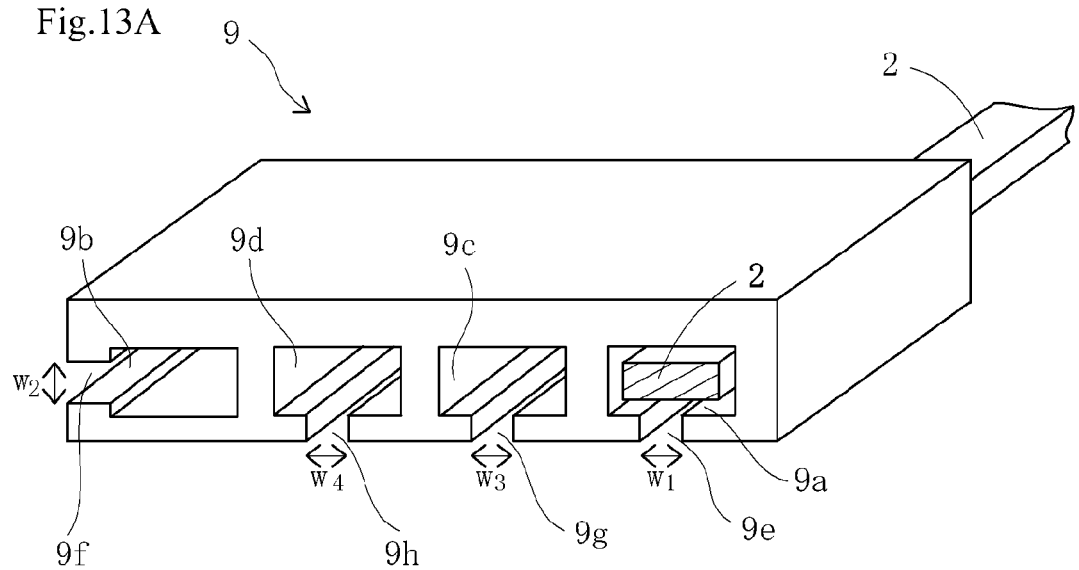
FIG. 13A and FIG. 13B are perspective views of a slider according to the fifth embodiment of the present invention.
Figure 13B:
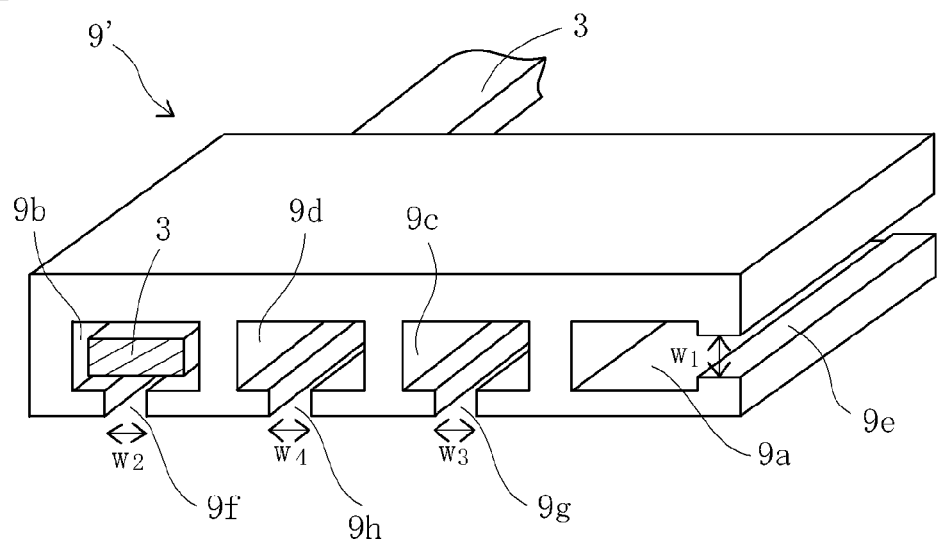

FIG. 13A is a perspective view of the slider 9, and FIG. 13B is a perspective view of the slider 9'. As shown in FIG. 13A, the slider 9 has the substantially same configuration as the slider 8 except for that a third through hole is composed of two independent through holes 9c, 9d (hereinafter referred to as third through holes 9c, 9d), and a third slit is composed of two independent slits 9g, 9h (hereinafter referred to as third slits 9g, 9h).

The slider 9 has: a first through hole 9a through which the first elastic wire 2 is to be inserted; a second through hole 9b through which the second elastic wire 3 is to be inserted; the third through hole 9c through which the third elastic wire 7 is to be inserted; the third through hole 9d through which the third elastic wire 7' is to be inserted; a first slit 9e which is communicated with the first through hole 9a; a second slit 9f which is communicated with the second through hole 9b; a third slit 9g which is communicated with the third through hole 9c; and a third slit 9h which is communicated with the third through hole 9d. That is, the slider 9 is configured such that the third through hole 9d and the third slit 9h are further formed in the slider 8. The slider 9' is configured such that the third through hole 9d and the third slit 9h are further formed in the slider 8'. The slider 9 and the slider 9' differ from each other only with respect to the position of the first slit 9e and the position of the second slit 9f.

The third through holes 9d formed in the sliders 9, 9' have rectangular cross sections (opening faces) which are one size larger than cross-sectional shapes of the third elastic wire 7' such that the sliders 9, 9' are smoothly slidable along the third elastic wire 7'. However, the long side of the third elastic wire 7' in a cross-sectional shape is longer than the short side of the third through hole 9d in a cross-sectional shape, and hence, the third elastic wire 7' is not rotatable in the third through hole 9d.

A width $w_4$ of the third slit 9h formed in the slider 9, 9' is longer than the short side of the third elastic wire 7' in a cross-sectional shape, and is shorter than the long side of the third elastic wire 7 in a cross-sectional shape. Further, the third slits 9h are formed on lower sides of the third through holes 9d (the long sides in a cross-sectional shape) respectively. Accordingly, it is neither possible to insert the third elastic wire 7' through the third through hole 9d, nor to takeout the third elastic wire 7' from the third through hole 9d through the third slit 9h.

Figure 14:
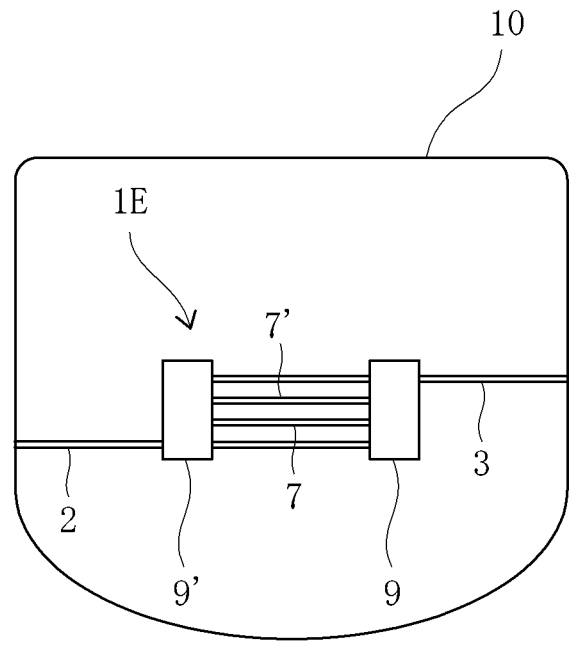
FIG. 14 is a plan view showing a mounting state of the deformed nail corrector according to the fifth embodiment.

FIG. 14 is a plan view of the deformed nail corrector 1E according to this embodiment in a state where the deformed nail corrector 1E is mounted on the deformed nail 10. As shown in FIG. 14, the third elastic wires 7, 7' are arranged between the first elastic wire 2 and the second elastic wire 3 in the length direction of the deformed nail 10. One end portion of the first elastic wire 2 is fixed to one edge of the deformed nail 10 in the width direction, and a portion of the first elastic wire 2 projecting out of the slider 9 on the other edge portion side is cut. One end portion of the second elastic wire 3 is fixed to the other edge of the deformed nail 10 in the width direction, and a portion of the second elastic wire 3 projecting out of the slider 9' on the other edge portion side is cut. The third elastic wires 7, 7' are arranged between the sliders 9, 9', and are not fixed to the deformed nail 10. Portions of the third elastic wires 7, 7' projecting out of an area between the sliders 9, 9' are cut.

The deformed nail corrector 1E according to this embodiment is mounted on the deformed nail 10 in accordance with the substantially same steps as the deformed nail corrector 1D according to the fourth embodiment.

To be more specific, the first elastic wire 2 and the second elastic wire 3 are bound to each other by the sliders 9, 9' and, thereafter, the third elastic wire 7 is to be inserted through the third through holes 9c formed in the sliders 9, 9' and, at the same time, the third elastic wire 7' is to be inserted through the third through holes 9d formed in the sliders 9, 9'. Due to such an operation, the third elastic wires 7, 7' are also bound by the sliders 9, 9', and hence, a state where the first elastic wire 2, the second elastic wire 3 and the third elastic wires 7, 7' are bent (deformed) along the deformed nail 10 is maintained. As a result, at both edges of the deformed nail 10, an elastic force is generated also by the third elastic wires 7, 7' in addition to elastic forces generated by the first elastic wire 2 and the second elastic wire 3.

According to the deformed nail corrector 1E according to this embodiment, compared to the deformed nail corrector 1D according to the fourth embodiment, an elastic force generated in the deformed nail 10 can be increased by an elastic force generated by the third elastic wire 7'. On the other hand, the elastic force of the deformed nail corrector 1E can be set to the substantially same level as the elastic force generated by the deformed nail corrector 1D by removing the third elastic wire 7', and the elastic force of the deformed nail corrector 1E can be set to the substantially same level as the elastic force generated by the deformed nail corrector 1B according to the second embodiment by removing the third elastic wire 7, 7'. That is, according to the deformed nail corrector 1E according to this embodiment, the third elastic wire 7, 7' can be removed or mounted depending on a state of the deformed nail 10, and hence, an elastic force generated in the deformed nail 10 can be adjusted over a wider range.

Sixth Embodiment

Figure 15:
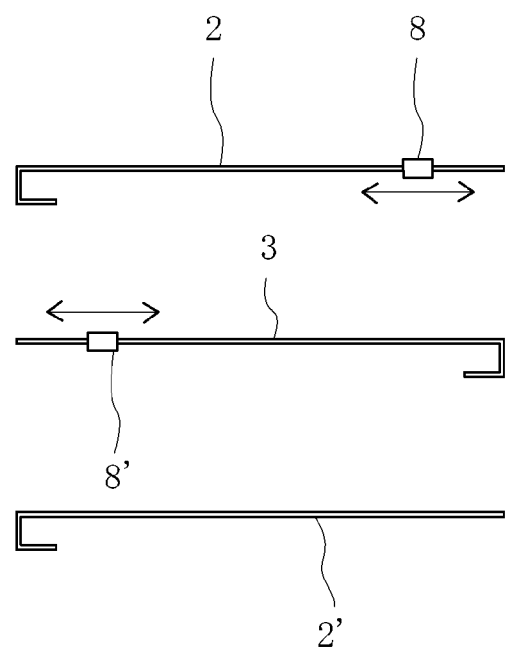
FIG. 15 is a view showing a deformed nail corrector according to a sixth embodiment of the present invention.

FIG. 15 shows a deformed nail corrector 1F according to a sixth embodiment of the present invention. As shown in FIG. 15, the deformed nail corrector 1F according to this embodiment has the substantially same configuration as the deformed nail corrector 1B according to the second embodiment except for that a first elastic wire is formed of two independent elastic wires 2, 2' (hereinafter referred to as first elastic wires 2, 2'), and the deformed nail corrector 1F includes sliders 8, 8' in place of the sliders 4, 4'.

Figure 16:
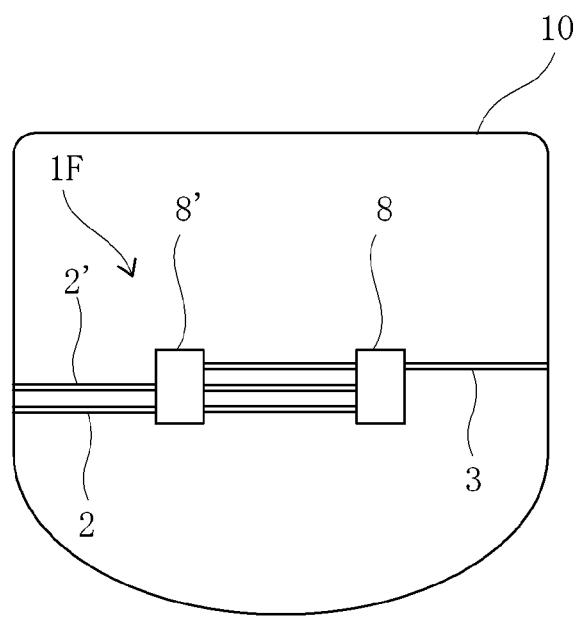
FIG. 16 is a plan view showing a mounting state of the deformed nail corrector according to the sixth embodiment.

FIG. 16 is a plan view of the deformed nail corrector 1F according to this embodiment in a state where the deformed nail corrector 1F is mounted on the deformed nail 10. As shown in FIG. 16, the first elastic wire 2' is arranged between the first elastic wire 2 and the second elastic wire 3 in the length direction of the deformed nail 10. One end portions of the first elastic wires 2, 2' are fixed to one edge of the deformed nail 10 in the width direction, and portions of the first elastic wires 2, 2' projecting out of the slider 8 on the other edge portion sides are cut. One end portion of the second elastic wire 3 is fixed to the other edge of the deformed nail 10 in the width direction, and a portion of the second elastic wire 3 projecting out of the slider 8' on the other edge portion side is cut.

In the deformed nail corrector 1F according to this embodiment, one end portions of the first elastic wires 2, 2' are fixed by being hooked to one edge of the deformed nail 10 in the width direction, and hence, an elastic force is generated at two places at one edge of the deformed nail 10 in the width direction. Accordingly, in the deformed nail corrector 1F according to this embodiment, the deformed nail 10 can be corrected over a relatively wide range.

Further, in the deformed nail corrector 1F according to this embodiment, an elastic force generated at one edge of the deformed nail 10 in the width direction is dispersed to two places as described above. Accordingly, compared to the deformed nail corrector 1B according to the second embodiment and the deformed nail corrector 1D according to the fourth embodiment where an elastic force is generated at one place, a risk that the deformed nail 10 is broken can be decreased.

In the deformed nail corrector 1F according to this embodiment, the first elastic wire 2 is to be inserted through the through hole 8a and the first elastic wire 2' is to be inserted through the through hole 8c, and hence, the through hole 8a and the through hole 8c constitute a first through hole, and the slit 8d and the slit 8f constitute a first slit.

[Modification]

Although preferred embodiments of the deformed nail corrector according to the present invention have been described heretofore, the present invention is not limited to the above-mentioned respective embodiments.

Figure 17:
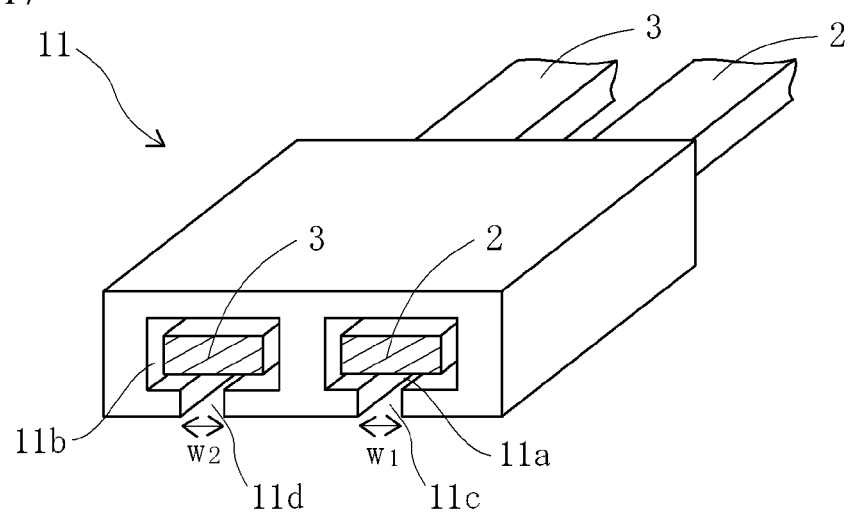
FIG. 17 is a view showing a modification of the slider used in the deformed nail correctors according to the first to third embodiments of the present invention.

For example, in the present invention, the number and the positions of the slits formed in the slider can be changed as desired. FIG. 17 shows a modification of the sliders 4, 4' used in the deformed nail correctors 1A to 1C according to the first to third embodiments. A slider 11 shown in FIG. 17 has, in the same manner as the sliders 4, 4', a first through hole 11a, a second through hole 11b, a first slit 11c communicated with the first through hole 11a, and a second slit 11d communicated with the second through hole 11b. A first elastic wire 2 is to be inserted through the first through hole 11a, and a second elastic wire 3 is to be inserted through the second through hole 11b. Accordingly, with the use of the slider 11, in mounting the deformed nail corrector according to the present invention, it is possible to save time and efforts necessary for binding the first elastic wire 2 and the second elastic wire 3 to each other. Further, a first slit 11c is formed on a lower side of the first through hole 11a and a second slit 11d is also formed on a lower side of the second though hole 11b. Accordingly, there is no possibility that the first elastic wire 2 is removed from the first through hole 11a through the first slit 11c and that the second elastic wire 3 is removed from the second through hole 11b through the second slit 11d.

Figure 18A:
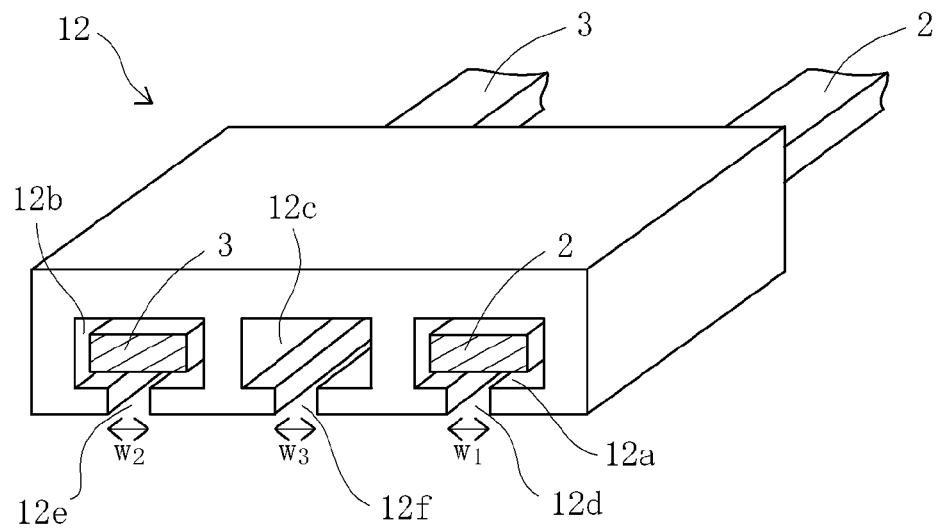
FIG. 18A and FIG. 18B are views showing a modification of the slider used in the deformed nail correctors according to the fourth to sixth embodiments of the present invention.
Figure 18B:
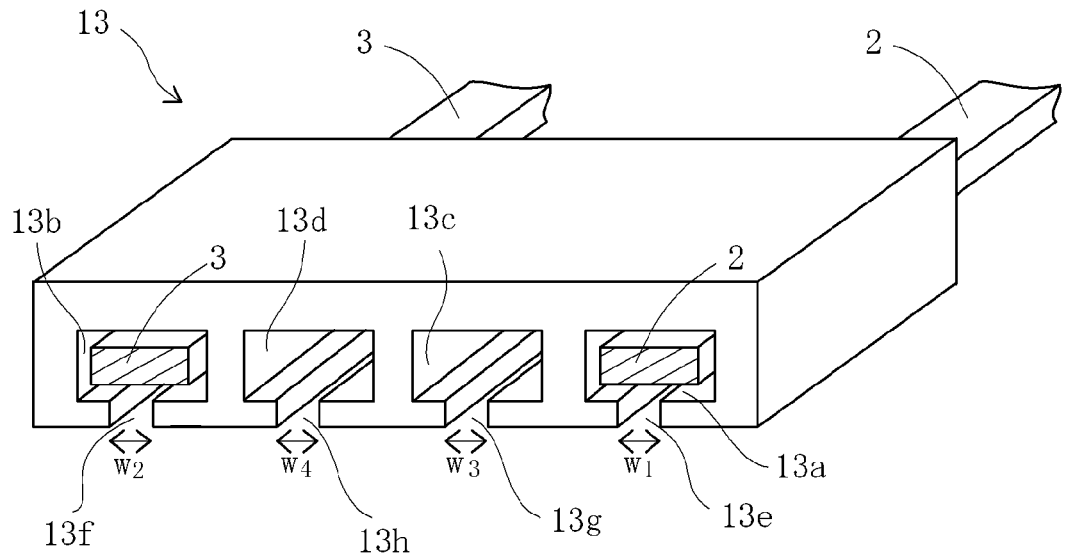

FIG. 18A shows a modification of the sliders 8, 8' used in the deformed nail correctors 1D, 1F according to the fourth and sixth embodiments, and FIG. 18B shows a modification of the sliders 9, 9' used in the deformed nail corrector 1E according to the fifth embodiment. With the use of sliders 12 (13) shown in FIG. 18A and FIG. 18B, it is possible to save time and efforts necessary for binding at least a first elastic wire 2 and a second elastic wire 3 to each other, and it is also possible to prevent the first elastic wire 2 from being removed from a first through hole 12a (13a) through a first slit 12d (13e) and to prevent a second elastic wire 3 from being removed from a second through hole 12b (13b) through a second slit 12e (13f).

Figure 19A:
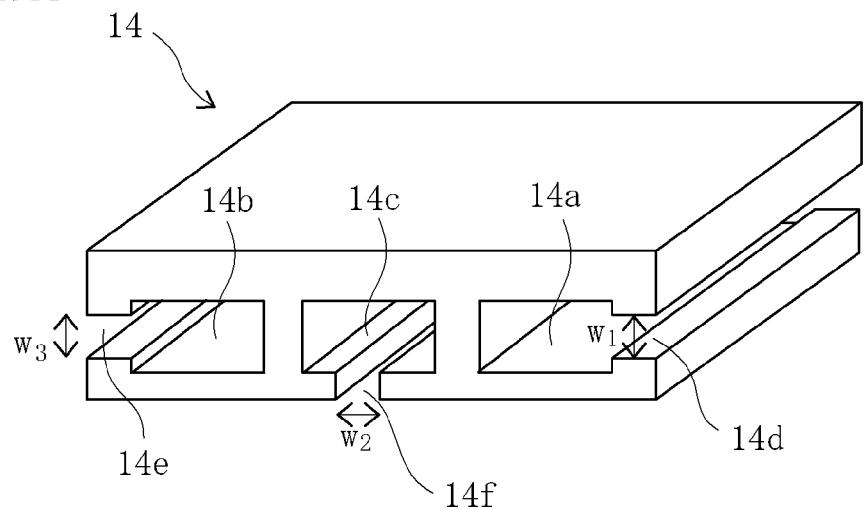
FIG. 19A and FIG. 19B are views showing another modification of the slider used in the deformed nail correctors according to the fourth to sixth embodiments of the present invention.
Figure 19B:
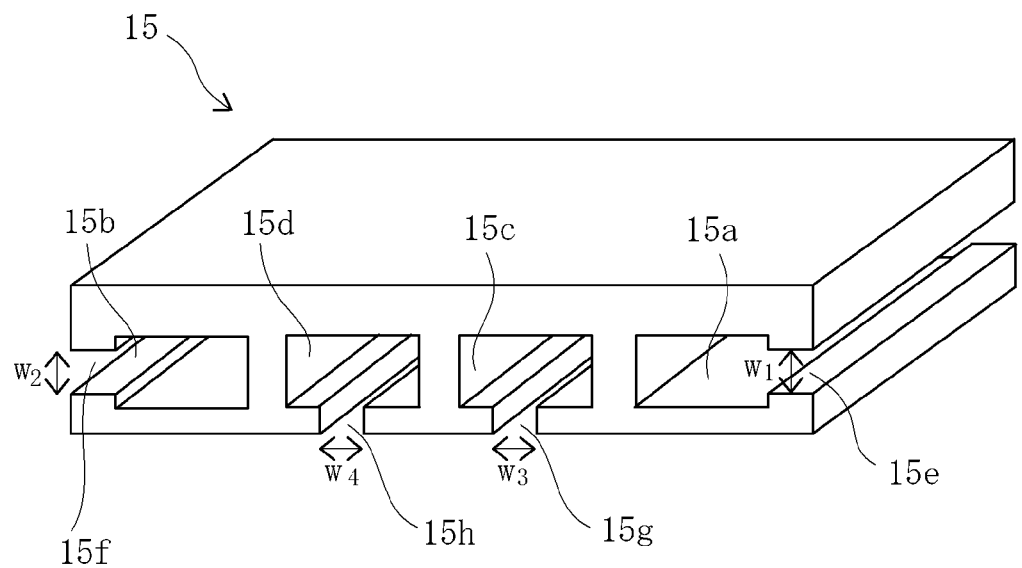

FIG. 19A shows another modification of the sliders 8, 8' used in the deformed nail correctors 1D, 1F according to the fourth and sixth embodiments, and FIG. 19B shows another modification of the sliders 9, 9' used in the deformed nail corrector 1E according to the fifth embodiment. With the use of sliders 14 (15) shown in FIG. 19A and FIG. 19B, the first elastic wire 2 can be inserted through the first through hole 14a (15a) or the first elastic wire 2 can be taken out from the first through hole 14a (15a) through the first slit 14d (15e). Further, the second elastic wire 3 can be inserted through the second through hole 14b (15b) or the second elastic wire 3 can be taken out from the second through hole 14b (15b) through the second slit 14e (15f). The sliders 12, 14 shown in FIG. 18A and FIG. 19A are provided as the modifications of the sliders 8, 8' used in the deformed nail correctors 1D, 1F according to the fourth and sixth embodiments, and the sliders 13, 15 shown in FIG. 18B and FIG. 19B are provided as the modifications of the sliders 9, 9' used in the deformed nail corrector 1E according to the fifth embodiment. However, these sliders 12 to 15 can be also used when necessary in deformed nail correctors 1G to 1L according to first to sixth modifications described later.

Figure 20A:
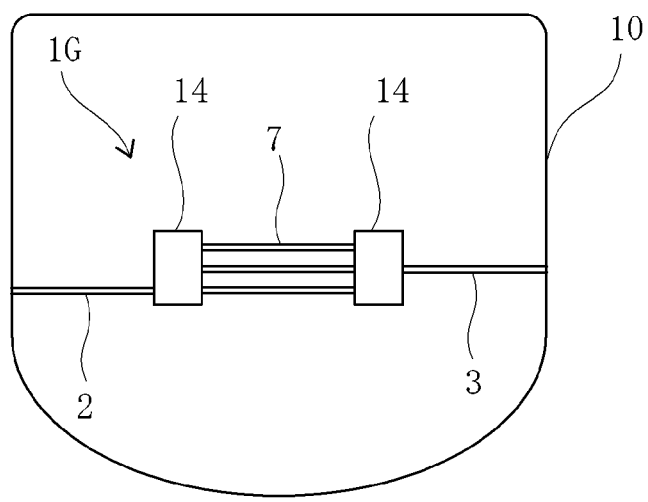
FIG. 20A to FIG. 20C are plan views showing a mounting state of the deformed nail corrector according to the first to third modifications of the present invention.
Figure 20B:
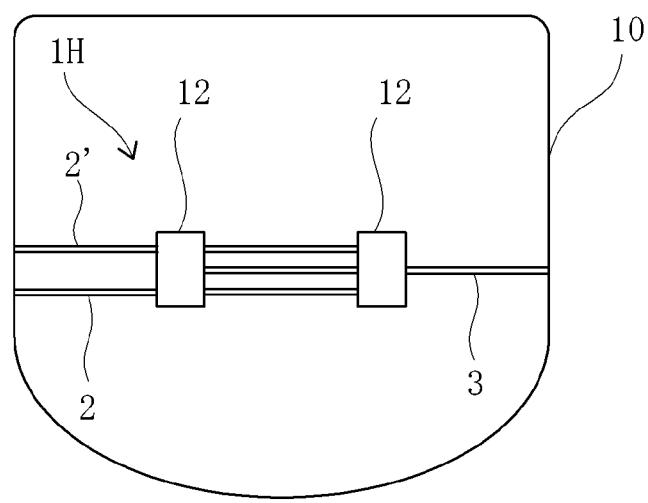
Figure 20C:
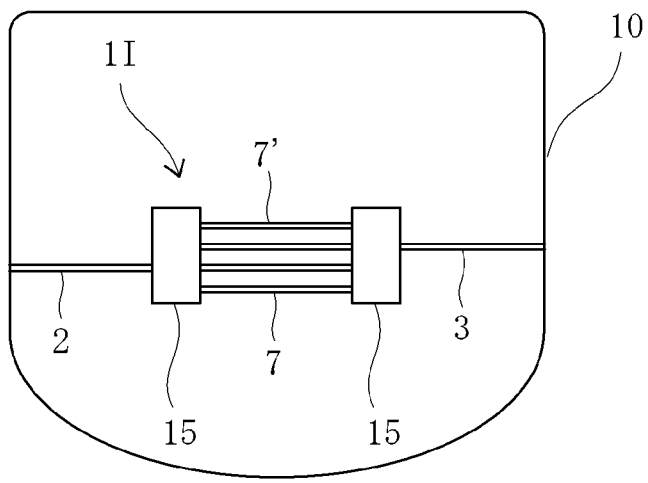

In the present invention, the arrangement in the length direction, the number and the combination of the elastic wires of the deformed nail 10 can be changed as desired. FIG. 20A to FIG. 20C are plan views of deformed nail correctors 1G to 1I according to the first to third modifications which are mounted on the deformed nails 10 respectively. As shown in FIG. 20A, in the deformed nail corrector 1G, a second elastic wire 3 is arranged between a first elastic wire 2 and a third elastic wire 7. As shown in FIG. 20B, in the deformed nail corrector 1H, a second elastic wire 3 is arranged between a first elastic wire 2 and a first elastic wire 2'. As shown in FIG. 20C, in the deformed nail corrector 1I, a first elastic wire 2 and a second elastic wire 3 are arranged between third elastic wires 7, 7'. In the deformed nail corrector 1G, the third elastic wire 7 can be removed from a third through hole 14b or the third elastic wire 7 can be inserted through the third through hole 14b through a third slit 14e formed in a slider 14, and hence, the third elastic wire 7 can be removed or mounted after the deformed nail corrector 1G is mounted on the deformed nail 10. In the same manner, in the deformed nail corrector 1I, third elastic wires 7, 7' can be removed from third through holes 15a, 15b and the third elastic wires 7, 7' can be inserted through the third through holes 15a, 15b through third slits 15e, 15f formed in the slider 15, and hence, the third elastic wires 7, 7' can be easily removed or mounted after the deformed nail corrector 1I is mounted on the deformed nail 10.

In the present invention, a slider having no slit can be used, and a slider made of a Ti—Al—V alloy, stainless steel, plastic or the like can be also used.

In the present invention, cross-sectional shapes of the first to third elastic wires and cross-sectional shapes of the through holes formed in the sliders can be changed to desired shapes such as an elliptical shape or an oblong circular shape. Although it is not always necessary to make cross-sectional shapes of the first to third elastic wires and cross-sectional shapes of the through holes have the same shape, it is desirable that the cross-sectional shapes of the first to third elastic wires and the cross-sectional shapes of the through holes are similar to each other such that the sliders are smoothly slidable along the first to third elastic wires.

Figure 21A:
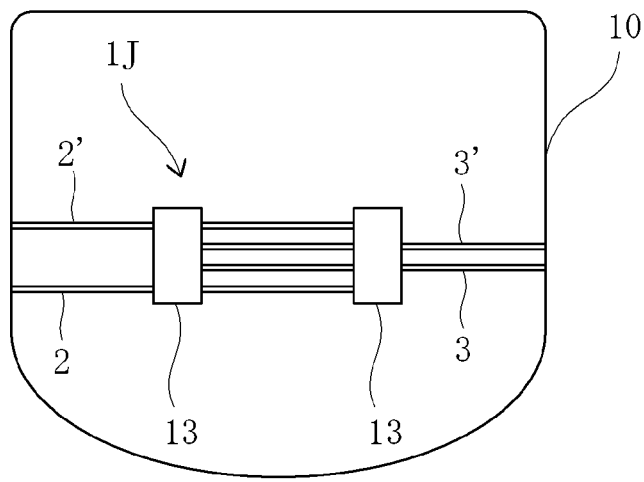
FIG. 21A to FIG. 21C are plan views showing a mounting state of the deformed nail corrector according to the fourth to sixth modifications of the present invention.
Figure 21B:
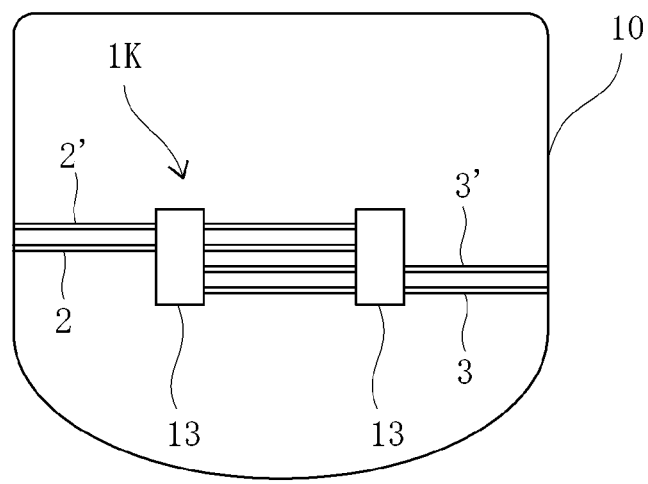
Figure 21C:
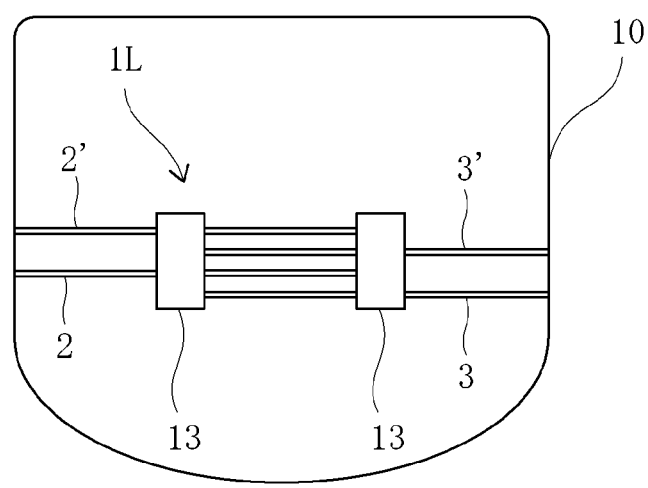

FIG. 21A to FIG. 21C are plan views of deformed nail correctors 1J to 1L according to fourth to sixth modifications where a second elastic wire is composed of two independent elastic wires 3, 3' (hereinafter referred to as second elastic wires 3, 3'). In the deformed nail corrector 1J, in the length direction of a deformed nail 10, the second elastic wires 3, 3' are arranged between a first elastic wire 2 and a first elastic wire 2'. In the deformed nail corrector 1K, first elastic wires 2, 2' are arranged on one side of a deformed nail 10 in the length direction, and second elastic wires 3, 3' are arranged on the other side of the deformed nail 10 in the length direction. In the deformed nail corrector 1L, in the length direction of a deformed nail 10, a first elastic wire 2 (2') and a second elastic wire 3 (3') are alternately arranged.

In the present invention, positions of through holes formed in sliders can be changed as desired. In the above-mentioned respective embodiments, the through holes are formed parallel to each other in the lateral direction (horizontal direction) so as to prevent the increase of a thickness of the slider. However, provided that the increase of a thickness of the slider is allowable to some extent, among a plurality of through holes, at least two through holes may be formed parallel to each other in the up and down direction (vertical direction), that is, in the thickness direction of the slider.

Figure 22A:
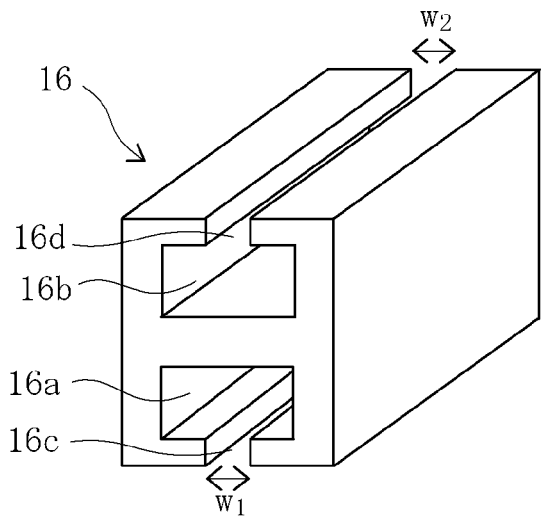
FIG. 22A to FIG. 22C are views showing another modification of the slider used in the deformed nail correctors according to the first to third embodiments of the present invention.
Figure 22B:
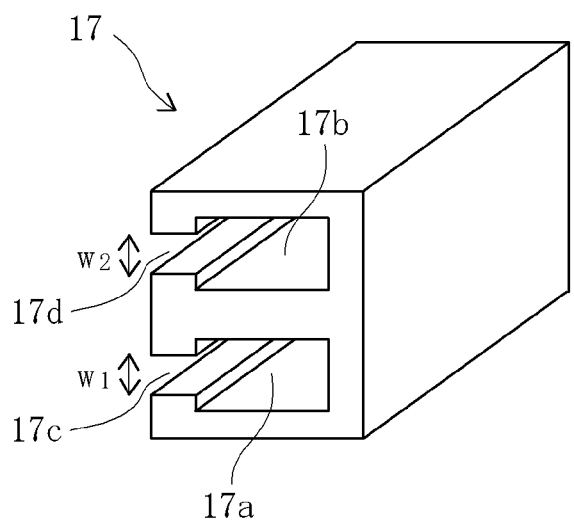
Figure 22C:
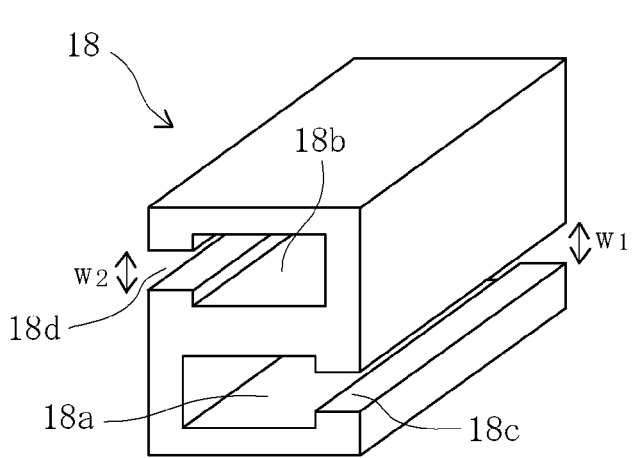

FIG. 22A to FIG. 22C show another modifications of the sliders 4, 4' used in the deformed nail correctors 1A to 1C according to the first to third embodiments. A slider 16 shown in FIG. 22A has: a first through hole 16a; a second through hole 16b formed above the first through hole 16a; a first slit 16c communicated with the first through hole 16a; and a second slit 16d communicated with the second through hole 16b. A material of the slider 16, sizes of the first through hole 16a and the second through hole 16b, a width $W_1$ of the first slit 16c, a width $w_2$ of the second slit 16d and the like are substantially equal to those of the sliders 4, 4', 11.

A slider 17 shown in FIG. 22B has: a first through hole 17a; a second through hole 17b formed above the first through hole 17a; a first slit 17c communicated with the first through hole 17a; and a second slit 17d communicated with the second through hole 17b. The slider 17 and the slider 16 differ from each other only with respect to the positions of the first slits 17c, 16c and the positions of the second slits 17d, 16d.

A slider 18 shown in FIG. 22C has: a first through hole 18a; a second through hole 18b formed above the first through hole 18a; a first slit 18c communicated with the first through hole 18a; and a second slit 18d communicated with the second through hole 18b. The slider 18 and the slider 17 differ from each other only with respect to the positions of the first slits 18c, 17c.

Figure 23A:
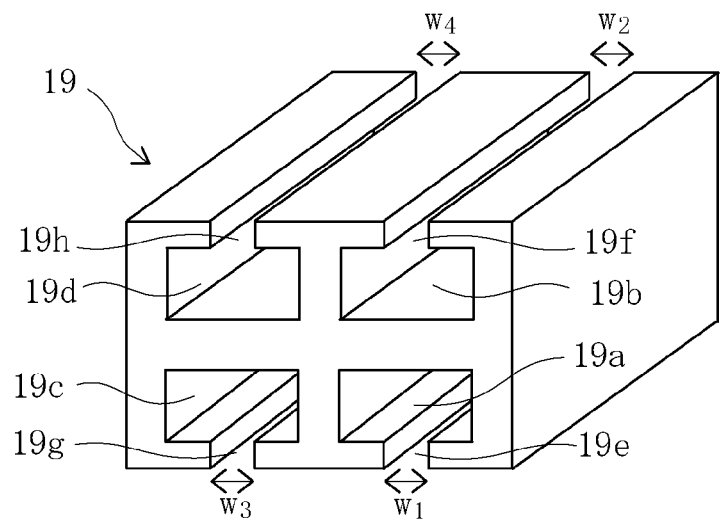
FIG. 23A and FIG. 23B are views showing still another modification of the slider used in the deformed nail correctors according to the fifth embodiment of the present invention.
Figure 23B:
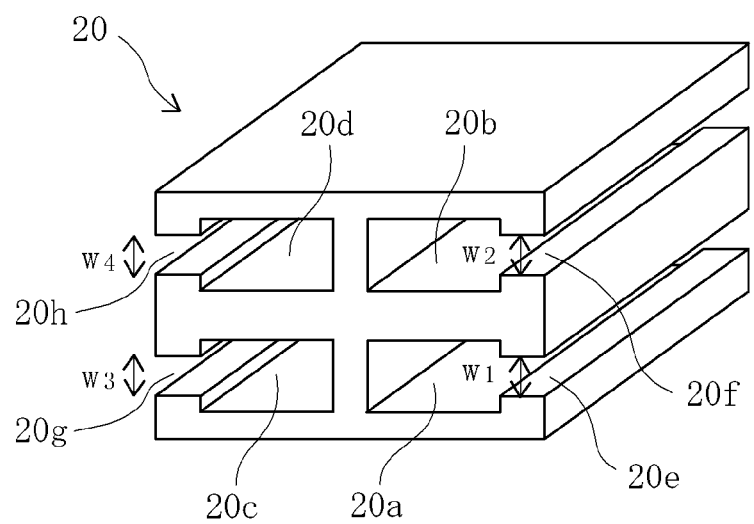

FIG. 23A and FIG. 23B show still further modifications of the sliders 9, 9' used in the deformed nail corrector 1E according to the fifth embodiment. A slider 19 shown in FIG. 23A has: a first through hole 19a; a second through hole 19b; third through holes 19c, 19d; a first slit 19e communicated with the first through hole 19a; a second slit 19f communicated with the second through hole 19b; a third slit 19g communicated with the third through hole 19c; and a third slit 19h communicated with the third through hole 19d. In the slider 19, the second through hole 19b is formed above the first through hole 19a, and the third through hole 19d is formed above the third through hole 19c. A material of the slider 19, sizes of the first through hole 19a to the third through holes 19d, widths $w_1$ to $w_4$ of the first to third slits 19e to 19h and the like are equal to those of the sliders 9, 9', 13, 15.

A slider 20 shown in FIG. 23B has: a first through hole 20a; a second through hole 20b; third through holes 20c, 20d; a first slit 20e communicated with the first through hole 20a; a second slit 20f communicated with the second through hole 20b; a third slit 20g communicated with the third through hole 20c; and a third slit 20h communicated with the third through hole 20d. In the slider 20, the second through hole 20b is formed above the first through hole 20a, and the third through hole 20d is formed above the third through hole 20c. The slider 20 and the slider 19 differ from each other only with respect to the positions of the respective slits 20e to 20h, 19e to 19h.

Figure 24A:
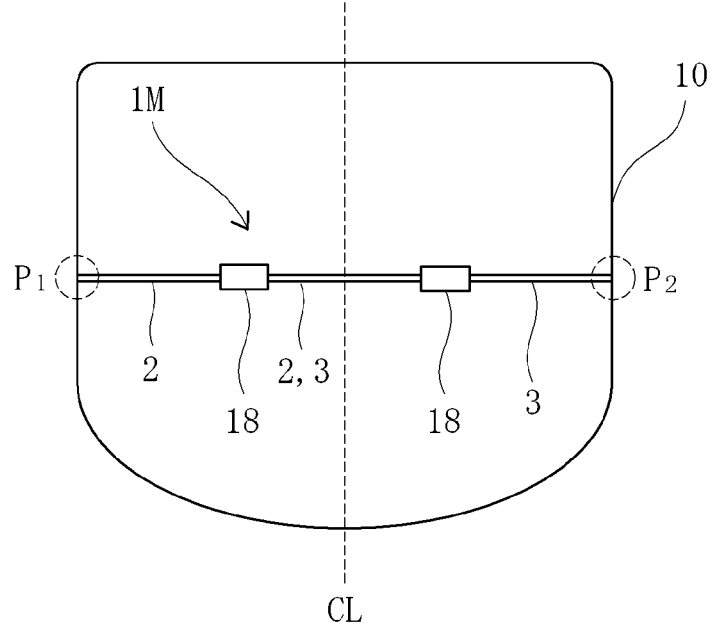
FIG. 24A and FIG. 24B are plan views showing a mounting state of the deformed nail corrector according to seventh and eighth modifications of the present invention.

FIG. 24A is a plan view showing a mounting state of a deformed nail corrector 1M according to a seventh modification provided with the slider 18 shown in FIG. 22C. In the deformed nail corrector 1M, the first elastic wire 2 and the second elastic wire 3 are bound to each other by the slider 18 where the first through hole 18a and the second through hole 18b are formed parallel to each other in the vertical direction. Accordingly, a fixing position $P_1$ of the first elastic wire 2 at one edge of the deformed nail 10 in the width direction and a fixing position $P_2$ of the second elastic wire 3 at the other edge of the deformed nail 10 in the width direction have the line symmetry relationship with respect to a center line CL of the deformed nail 10 in the width direction. Accordingly, in the deformed nail corrector 1M, elastic forces can be generated at line symmetry positions with respect to the center line CL in the width direction, and hence, elastic forces can be applied to the deformed nail 10 uniformly at left and right sides by arranging the respective sliders 18 at positions which are the same distance away from the center line CL in the width direction. As a result, the deformed nail 10 can be corrected more accurately. In the deformed nail corrector 1M, the slider 16 or the slider 17 may be used in place of the slider 18.

Figure 24B:
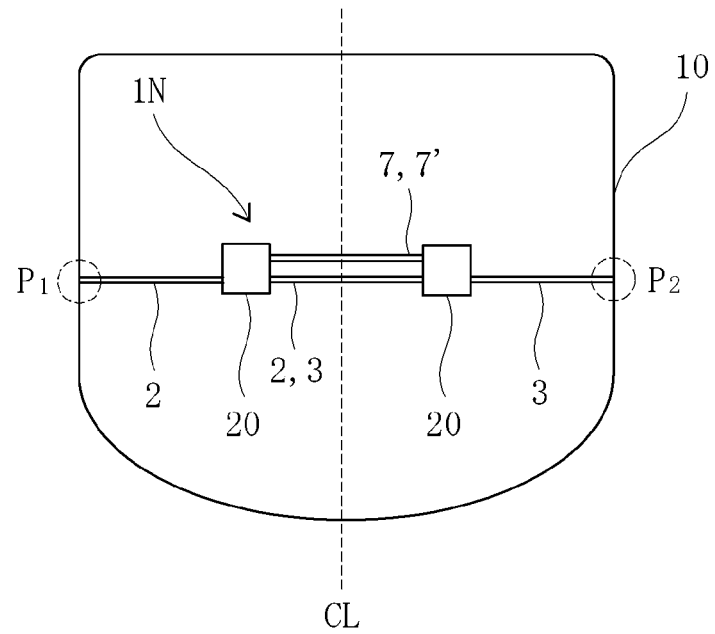

FIG. 24B is a plan view showing a mounting state of a deformed nail corrector 1N according to an eighth modification provided with the slider 20 shown in FIG. 23B. Also in the deformed nail corrector 1N, a fixing position $P_1$ of the first elastic wire 2 at one edge of the deformed nail 10 in the width direction and a fixing position $P_2$ of the second elastic wire 3 at the other edge of the deformed nail 10 in the width direction have the line symmetry relationship with respect to a center line CL of the deformed nail 10 in the width direction. Accordingly, elastic forces can be applied to the deformed nail 10 uniformly at left and right sides by arranging the respective sliders 20 at positions which are the same distance away from the center line CL in the width direction. As a result, the deformed nail 10 can be corrected more accurately. In the deformed nail corrector 1N, third elastic wires 7, 7' are to be inserted through the third through holes 20c, 20d respectively, the first elastic wire 2' and the second elastic wire 3' may be inserted through the third through holes 20c, 20d in place of the third elastic wires 7, 7'. In such a case, the fixing position of the first elastic wire 2' at one edge of the deformed nail 10 in the width direction and the fixing position of the second elastic wire 3' at the other edge of the deformed nail 10 in the width direction also have the line symmetry relationship with respect to a center line CL of the deformed nail 10 in the width direction. Further, in the deformed nail corrector 1N, the slider 19 may be used in place of the slider 20.

In the present invention, the binding means may include three or more sliders.

In the present invention, provided that an elastic force can be generated at one edge of the deformed nail 10 in the width direction or at the other edge of the deformed nail 10 in the width direction, a material of the first to third elastic wires can be changed as desired. For example, the first to third elastic wires made of a Ti—Al—Nb alloy or a Ni—Ti alloy can be used. When the first to third elastic wires made of a super elastic alloy such as a Ni—Ti alloy are used, it is necessary to adjust an elastic force such that the deformed nail 10 is not excessively corrected. As a matter of course, among the first to third elastic wires, a material of only at least one elastic wire may be changed.

In the present invention, the shape of one end portion of the first elastic wire and the shape of one end portion of the second elastic wire may be changed as desired provided that these end portions are formed in shapes such that the end portions can be fixed to one edge and the other edge of the deformed nail 10 in the width direction respectively. Shapes of the first to third elastic wires per se may be changed into shapes other than a straight linear shape such as a curved shape along the deformed nail 10. Further, to prevent the slider from being removed from the other end portion of the first elastic wire or to prevent the slider from being removed from the other end portion of the second elastic wire in a state where the corrector is not mounted on the deformed nail, the other end portions of the first elastic wire and the second elastic wire may be folded or working such as working which increases diameters of the other end portions of the first elastic wire and the second elastic wire may be applied to the other end portions of the first elastic wire and the second elastic wire. In the same manner, working may be applied to both end portions of the third elastic wire.

In the present invention, the first elastic wire may include three or more independent elastic wires, the second elastic wire may include three or more independent elastic wires, or the third elastic wire may include three or more independent elastic wires.

In the present invention, the first to third elastic wires may include five or more elastic wires, and the number of through holes formed in the slider may be set to five or more. It is not always necessary that the number of elastic wires and the number of through holes agree with each other. For example, when a plurality of elastic wires which can be used as the third elastic wire are provided for suitably exchanging the third elastic wire depending on a state of the deformed nail 10, the number of elastic wires becomes larger than the number of through holes.

In the present invention, the first elastic wire or the second elastic wire can be used as the third elastic wire by cutting one end portion of the first elastic wire or the second elastic wire. Further, the third elastic wire can be used as the first elastic wire or the second elastic wire by folding one end portion of the third elastic wire.

In the above-mentioned respective embodiments, one end portion of the first elastic wire is fixed to one edge of the deformed nail 10 in the width direction and one end portion of the second elastic wire is fixed to the other edge of the deformed nail 10 in the width direction and, thereafter, the first elastic wire and the second elastic wire are bound to each other by the slider. However, it may be also possible that the first elastic wire and the second elastic wire are bound to each other by the slider and, thereafter, one end portion of the first elastic wire is fixed to one edge of the deformed nail 10 in the width direction and one end portion of the second elastic wire is fixed to the other edge of the deformed nail 10 in the width direction.

In the above-mentioned respective embodiments, to shorten a correction period of the deformed nail 10, a nail softening agent is applied to the deformed nail 10 by coating before the deformed nail corrector is mounted on the deformed nail 10. However, the deformed nail 10 may be corrected without applying the nail softening agent to the deformed nail 10.

DESCRIPTION OF REFERENCE SIGNS 1A to 1N deformed nail corrector
2, 2', 5 first elastic wire
3, 3', 6 second elastic wire
7, 7' third elastic wire
4, 4', 8, 8', 9, 9', 11 to 20 slider
10 deformed nail

The invention claimed is:

1. A deformed nail corrector for correcting a deformed nail, the deformed nail corrector comprising:
　a first elastic wire which has one end portion thereof fixable to one edge of the deformed nail in a width direction;
　a second elastic wire which has one end portion thereof fixable to the other edge of the deformed nail in the width direction; and
　two or more sliders which bind the first and second elastic wires to each other and are slidable along the first and second elastic wires in a bound state,
　wherein the first and second elastic wires are brought into a state where the first and second wires are deformed along the deformed nail in a corrector mounting state where said one end portion of the first elastic wire is fixable to said one edge of the deformed nail in the width direction, said one end portion of the second elastic wire is fixable to said the other edge of the deformed nail in the width direction, and the first and second elastic wires are bound to each other by the two or more sliders, and
　wherein the two or more sliders are slidable independently from each other along the first and second elastic wires in the corrector mounting state.

2. The deformed nail corrector according to claim 1, wherein each slider has:
　a first through hole through which the first elastic wire is to be inserted; and
　a second through hole through which the second elastic wire is to be inserted.

3. The deformed nail corrector according to claim 2, wherein the slider has: a first slit which is communicated with the first through hole, the first slit enabling fixing of the slider to the first elastic wire in the corrector mounting state; and
　a second slit which is communicated with the second through hole, the second slit enabling fixing of the slider to the second elastic wire in the corrector mounting state, and
　the first elastic wire is inserted into the inside of the first through hole through the first slit or the second elastic wire is inserted into the inside of the second through hole through the second slit.

4. The deformed nail corrector according to claim 2, wherein the first elastic wire is formed of two or more independent elastic wires, and
　the first through hole is formed of two or more independent through holes through which the respective elastic wires of the first elastic wire are to be inserted.

5. The deformed nail corrector according to claim 4, wherein the second elastic wire is formed of two or more independent elastic wires, and
　the second through hole is formed of two or more independent through holes through which the respective elastic wires of the second elastic wire are to be inserted.

6. The deformed nail corrector according to claim 1, wherein said one end portion of the first elastic wire and said one end portion of the second elastic wire may be folded in a hook shape.

7. The deformed nail corrector according to claim 2, wherein the deformed nail corrector further includes a third elastic wire whose both end portions are not fixable to one edge of the deformed nail in the width direction or the other edge of the deformed nail in the width direction, the slider further has a third through hole through which the third elastic wire is to be inserted, and the first, second and third elastic wires are brought into a state where the first, second and third wires are deformed along the deformed nail in a corrector mounting state where said one end portion of the first elastic wire is fixable to one edge of the deformed nail in the width direction, said one end portion of the second elastic wire is fixable to the other edge of the deformed nail in the width direction, and the first, second and third elastic wires are bound to each other by the slider.

8. The deformed nail corrector according to claim 7, wherein the slider has a third slit which is communicated with the third through hole, the third slit enabling fixing of the slider to the third elastic wire in the corrector mounting state.

9. The deformed nail corrector according to claim 8, wherein the third elastic wire is to be inserted through the third through hole through the third slit.

10. The deformed nail corrector according to claim 7, wherein the third elastic wire is arranged between the first elastic wire and the second elastic wire in a length direction of the deformed nail in the corrector mounting state.

11. The deformed nail corrector according to claim 7, wherein the first elastic wire is arranged between the second elastic wire and the third elastic wire in a length direction of the deformed nail in the corrector mounting state.

12. The deformed nail corrector according to claim 7, wherein the third elastic wire is formed of two or more independent elastic wires, and the third through hole is formed of two or more independent through holes through which the respective elastic wires of the third elastic wire are to be inserted.

13. The deformed nail corrector according to claim 12, wherein the first and second through holes are formed parallel to each other in a thickness direction of the slider, said two or more independent through holes which constitute the third through hole are formed parallel to each other in the thickness direction, and the first through hole, the second through hole and said two or more independent through holes are arranged parallel to each other in a direction orthogonal to the thickness direction.

14. The deformed nail corrector according to claim 2, wherein the first and second through holes are formed parallel to each other in a thickness direction of the slider.

* * * * *